US012723228B2

(12) United States Patent
Chen

(10) Patent No.: US 12,723,228 B2
(45) Date of Patent: Sep. 1, 2026

(54) DIFFERENTIAL FLOW MICRO-VALVE SAMPLING IN INTEGRATED SENSOR PLATFORM FOR CELL OR TISSUE CULTURE AND ANALYSIS

(71) Applicant: Colorado State University Research Foundation, Fort Collins, CO (US)

(72) Inventor: Thomas Chen, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 912 days.

(21) Appl. No.: 17/965,989

(22) Filed: Oct. 14, 2022

(65) Prior Publication Data

US 2023/0117156 A1 Apr. 20, 2023

Related U.S. Application Data

(60) Provisional application No. 63/255,578, filed on Oct. 14, 2021.

(51) Int. Cl.

| | |
|---|---|
| ***C12M 1/00*** | (2006.01) |
| ***B01L 3/00*** | (2006.01) |
| ***C12M 1/26*** | (2006.01) |
| ***C12M 1/34*** | (2006.01) |
| ***G01N 27/416*** | (2006.01) |

(52) U.S. Cl.

CPC ............ *C12M 41/34* (2013.01); *C12M 23/40* (2013.01); *C12M 33/12* (2013.01); *C12M 41/26* (2013.01); *G01N 27/416* (2013.01)

(58) Field of Classification Search

CPC ........................ B01L 2300/0645; C12M 23/40

See application file for complete search history.

(56) References Cited

U.S. PATENT DOCUMENTS 6,653,124 B1 * 11/2003 Freeman ............. F16K 99/0001 435/297.1

11,346,805 B2 5/2022 Chen et al.

2005/0158781 A1 * 7/2005 Woudenberg ..... B01L 3/502715 435/287.2

2006/0154361 A1 * 7/2006 Wikswo ................. C12M 23/16 435/297.5

2010/0105029 A1 * 4/2010 Ririe .................... C12Q 1/6844 435/6.12

(Continued)

OTHER PUBLICATIONS

Armbruster et al., "Limit of Blank, Limit of Detection and Limit of Quantitation," The Clinical Biochemist Reviews, Aug. 2008, vol. 29, Suppl. 1, pp. S49-S52.

(Continued)

*Primary Examiner* — Nathan A Bowers

(74) *Attorney, Agent, or Firm* — Meunier Carlin & Curfman LLC

(57) ABSTRACT

Electrochemical sensing devices and methods of using thereof employs a set of one or more sensor-integrated sampling wells or containers that operates with a pressure differential micro-valve to move controlled volume of sampled fluid within a controlled cell-growing environment. The differential micro-valve can be integrated into an instrumented well having one or more sensors to provide a high-throughput smart well plate platform for use in automation operation in diagnostics and drug discovery.

21 Claims, 14 Drawing Sheets

(56) References Cited

U.S. PATENT DOCUMENTS

| | | | | |
|---|---|---|---|---|
| 2011/0229927 A1* | 9/2011 | Larsen | C12M 41/34 | |
| | | | 435/287.1 | |
| 2015/0004077 A1* | 1/2015 | Wikswo | C12M 21/08 | |
| | | | 422/502 | |
| 2020/0324289 A1 | 10/2020 | Chen et al. | | |
| 2021/0094034 A1* | 4/2021 | Lee | C12M 23/16 | |
| 2021/0318286 A1 | 10/2021 | Chen et al. | | |
| 2023/0058647 A1* | 2/2023 | Cirit | C12M 29/24 | |

OTHER PUBLICATIONS

Bienert et al., "Membrane transport of hydrogen peroxide," Biochimica et Biophysica Acta (BBA)—Biomembranes, Aug. 2006, vol. 1758, Issue 8, pp. 994-1003.

Boveris et al., "The Mitochondrial Generation of Hydrogen Peroxide: General properties and effect of hyperbaric oxygen," Biochemical Journal, Jul. 1973, vol. 134, No. 3, pp. 707-716.

Dikalov et al., "Methods for Detection of Mitochondrial and Cellular Reactive Oxygen Species," Antioxidants & Redox Signaling, Jan. 2014, vol. 20, No. 2, pp. 372-382.

Heim et al., "Tissue-specific seasonal changes in mitochondrial function of a mammalian hibernator," American Journal of Physiology-Regulatory, Integrative and Comparative Physiology, Aug. 2017, vol. 313, Issue 2, pp. R180-R190.

Komlo'di et al., "Comparison of Mitochondrial Incubation Media for Measurement of Respiration and Hydrogen Peroxide Production," in: Palmeira, C., Mitochondrial Bioenergetics. Methods in Molecular Biology, Humana Press, New York, NY, May 2018, pp. 137-155.

Kornfeld et al., "Mitochondrial Reactive Oxygen Species at the Heart of the Matter: New Therapeutic Approaches for Cardiovascular Diseases," Circulation Research, May 2015, vol. 116, Issue 11, pp. 1783-1799.

Krumschnabel et al., "Simultaneous High-Resolution Measurement of Mitochondrial Respiration and Hydrogen Peroxide Production," in: Weissig, V., Mitochondrial Medicine: Methods in Molecular Biology, Humana Press, New York, NY, Jan. 2015, pp. 245-261.

Li et al., "Immune effects of glycolysis or oxidative phosphorylation metabolic pathway in protecting against bacterial infection," Journal of Cellular Physiology, Nov. 2019, vol. 234, Issue 11, pp. 20298-20309.

Loponte et al., "The Many Facets of Tumor Heterogeneity: Is Metabolism Lagging Behind?," Cancers, Oct. 2019, vol. 11, No. 10, 22 pages.

Makrecka-Kuka et al., "High-Resolution Respirometry for Simultaneous Measurement of Oxygen and Hydrogen Peroxide Fluxes in Permeabilized Cells, Tissue Homogenate and Isolated Mitochondria," Biomolecules, Jun. 2015, vol. 5, No. 3, pp. 1319-1338.

Murphy, Michael P et al., "How mitochondria produce reactive oxygen species," Biochemical Journal, Jan. 2009, vol. 417, Issue 1, 13 pages.

Nishikawa et al., "Impact of Mitochondrial ROS Production in the Pathogenesis of Diabetes Mellitus and Its Complications," Antioxidants & Redox Signaling, Feb. 2007, vol. 9, No. 3, pp. 343-353.

Obeidat et al., "A Multi-Sensor System for Measuring Bovine Embryo Metabolism," Author Manuscript, Biosensors and Bioelectronics, Feb. 2019, vol. 126, pp. 615-623.

Obeidat et al., "Characterization of an $O_2$ Sensor Using Microelectrodes," IEEE Sensors, 2016, 3 pages.

Obeidat et al., "Design of a Multi-Sensor Platform for Integrating Extracellular Acidification Rate with Multi-Metabolite Flux Measurement for Small Biological Samples," Biosensors and Bioelectronics, May 2019, vol. 133, pp. 39-47.

Obeidat et al., "Monitoring Oocyte/Embryo Respiration Using Electrochemical-Based Oxygen Sensors," Sensors and Actuators B: Chemical, Dec. 2018, vol. 276, pp. 72-81.

Peng et al., "Metabolic Reprogramming and Reactive Oxygen Species in T Cell Immunity," Frontiers in Immunology, Mar. 2021, vol. 12, Article No. 652687, 10 pages.

Puma et al., "Experimental oxygen concentration influences rates of mitochondrial hydrogen peroxide release from cardiac and skeletal muscle preparations," American Journal of Physiology-Regulatory, Integrative and Comparative Physiology, May 2020, vol. 318, Issue 5, pp. R972-R980.

Starkov, A.A. et al., "Measurement of mitochondrial ROS production," Manuscript in: Bross, P., Protein Misfolding and Cellular Stress in Disease and Aging. Methods in Molecular Biology, Humana Press, Totowa, NJ, Aug. 2010, pp. 245-255.

Tatsuma et al., "Peroxidase-Incorporated Polypyrrole Membrane Electrodes," Analytical Chemistry, May 1992, vol. 64, No. 10, pp. 1183-1187.

Wang et al., "Oxidative stress and mitochondrial dysfunction in Alzheimer's disease," Biochimica et Biophysica Acta (BBA)—Molecular Basis of Disease, Aug. 2014, vol. 1842, Issue 8, pp. 1240-1247.

Wong et al., "Production of superoxide and hydrogen peroxide from specific mitochondrial sites under different bioenergetic conditions," Journal of Biological Chemistry, Oct. 2017, vol. 292, Issue 41, pp. 16804-16809.

Zhang et al., "Identification of Discriminating Metabolic Pathways and Metabolites in Human PBMCs Stimulated by Various Pathogenic Agents," Frontiers in Physiology, Feb. 2018, vol. 9, Article 139, 13 pages.

Zheng, Jie, "Energy metabolism of cancer: Glycolysis versus oxidative phosphorylation (Review)," Oncology Letters, Dec. 2012, vol. 4, No. 6, pp. 1151-1157.

* cited by examiner 200a
210
214
241
212
244a
244
244b
242
250
243
246
248
254
238
252

200b
252'

200c
243'

542
541

DIFFERENTIAL FLOW MICRO-VALVE SAMPLING IN INTEGRATED SENSOR PLATFORM FOR CELL OR TISSUE CULTURE AND ANALYSIS

CROSS-REFERENCE TO RELATED APPLICATIONS

The application claims the benefit of U.S. Provisional Application No. 63/255,578, filed Oct. 14, 2021, entitled "Differential Flow Micro-Valve," which is hereby incorporated herein by reference in its entirety.

STATEMENT REGARDING FEDERALLY SPONSORED RESEARCH OR DEVELOPMENT

This invention was made with government support under grant R21 HD097601 awarded by National Institutes of Health. The government has certain rights in the invention.

BACKGROUND

The determination of various cellular metabolic parameters, such as oxygen consumption rate (OCR) and extracellular acidification (ECAR), is helpful in the understanding of bioenergetics in health and disease. Abnormal cellular bioenergetics has been associated with diseases such as obesity, diabetes, cancer, neurodegeneration, and cardiomyopathy, for example. Mitochondrial respiration and glycolytic metabolism can be estimated by measuring changes in dissolved oxygen and pH. However, OCR does not provide direct information about cellular substrate utilization, and ECAR can result from both glycolysis and oxidative metabolism. OCR and ECAR data alone may provide misleading results. Thus, co-measurement of other critical analytes, such as extracellular glucose and lactate flux, along with OCR and ECAR, may provide further insight into cellular metabolic processes.

Optical techniques, including florescence imaging, can typically be used for separately measuring analytes of interest discussed above. Optical measurement systems for imaging multiple samples typically include a plurality of wells seeded with a volume of cells and a single microscope that moves between each sample at predetermined intervals for imaging. Thus, such systems are not designed for real-time, single-cell, or simultaneous multiple analyte measurements. Even though it is possible to devise multiple optical sensors for multiple wells for simultaneously measuring florescent/photobleaching intensity, such systems are typically very expensive. Existing electrochemical techniques also do not incorporate multi-analyte measurement seamlessly in a highly integrated and compact system.

An Integrated Sensor Platform for Real-Time Cell/Tissue Analysis has been explored that employs electrochemical sensors in a traditional well-plate format to measure metabolic markers. It can provide instantaneous views of multi-analytes to gain a better understanding of cell/tissue behavior. It has a far-reaching impact on the research and development of new drugs for cancer, obesity, fertility, micro-dialysis, etc. When used for an extended period of time, electrochemical sensors integrated into the cell culture growing platform can be affected by fowling that may form in the cell culture environment. On-going measurements over a period of time can lead to the build-up or fowling of the real-time measurement environment.

Accordingly, a need exists for on-going, real-time, single- and/or multi-cell, and simultaneous multiple analyte measurements in a highly integrated system that can be easily incorporated into the existing medical/biological technology ecosystem.

SUMMARY

Provided herein are electrochemical sensing devices and methods of using thereof that employ a set of one or more sensor-integrated sampling wells or containers that operates with a pressure differential micro-valve to move a controlled volume of a fluid within a controlled cell- or tissue-growing environment. In some embodiments, the electrochemical sensing device is configured as a smart well plate in which a solution volume from each well is extracted, using a differential micro-valve, for automated monitoring of target analytes or measurands. The differential micro-valve can be integrated into an instrumented well having one or more sensors to provide a high-throughput smart well plate platform for use in automation operations in diagnostics and drug discovery.

In some embodiments, the differential micro-valve is configured to operate with no mechanical moving parts to improve reliability and avoid mechanical moving parts, which tend to break easily over time, especially at a micro-scale level. To reduce or prevent fluidic leakage through the differential micro-valve at the valve idle state, the differential micro-valve may include a thin, flexible membrane, such as a rubber membrane (e.g., membrane with PDMS), with flapped pin-holes. The volume dispensed by the differential micro-valve can be controlled by the application of the pressure to draw the sample through the differential micro-valve, e.g., via discrete actions by the vacuum pump, eliminating additive errors in any potentially long dispensing process. The negative pressure can be applied simultaneously across several channels each configured with the differential micro-valves. The differential micro-valve operation can mimic the mechanism and functionality of individual droplet movement achievable using digital microfluidics technology but without the issues associated with digital microfluidics.

In an aspect, an electrochemical sensing device is disclosed comprising one or more substrates joined to form a culture container configured to retain an electrochemical sample, the one or more substrates forming a bottom surface and a side wall surface for the culture container that terminates at a top to define the culture container; a sample container in operative connection with the culture container through a first channel defined in the one or more substrates, the one or more substrates forming a second bottom surface and a second side wall surface that terminates at a second top to define the sample container, wherein the first channel has a cross-sectional area at a first end that expands to form the sample container and has a cross-sectional area at a second end that expands to form the culture container; and a port in operative connection with the sample container through a second channel defined in the one or more substrates, wherein application of a negative pressure, at the port, different from the culture container, causes a portion of the electrochemical sample to flow from the culture container through the first channel to the sample container.

In some embodiments, the one or more substrates comprise a first section (e.g., layer) comprising at least one sensor or electrode embedded therein, the at least one sensor or electrode embedded therein being located below the culture container, the sample container, or a combination thereof; and a second section (e.g., layer) comprising microfluidic components defining the culture container, the first channel, and the sample container.

In some embodiments, the one or more substrates further form a second sample container in operative connection with the culture container through a third channel defined in the one or more substrates, the one or more substrates forming a third bottom surface and a third side wall surface that terminates at a third top to define the second sample container, wherein the third channel has a cross-sectional area at a first end that expands to form the second sample container and has a cross-sectional area at a second end that expands to form the culture container.

In some embodiments, the second sample container connects to a fourth channel defined in the one or more substrates, wherein the application of the negative pressure at the port causes a second portion of the electrochemical sample to flow from the culture container through the third channel to the second sample container.

In some embodiments, the one or more substrates further form a third sample container in operative connection with the culture container through a fifth channel defined in the one or more substrates, the one or more substrates forming a fourth bottom surface and a fourth side wall surface that terminates at a fourth top to define the third sample container, wherein the fifth channel has a cross-sectional area at a first end that expands to form the third sample container and has a cross-sectional area at a second end that expands to form the culture container.

In some embodiments, the one or more substrates further form a second culture container to retain a second electrochemical sample and a set of one or more sample containers coupled to the second culture container.

In some embodiments, the one or more substrates further form a third culture container to retain a third electrochemical sample and a set of one or more sample containers coupled to the third culture container.

In some embodiments, the electrochemical sensing device further includes a stimulus signal generation module comprising a stimulus signal generator circuit in communication with a controller circuit, the stimulus signal generator circuit being configured to generate a stimulus signal for conducting electrochemical analyses of the electrochemical sample.

In some embodiments, the electrochemical sensing device further includes a data acquisition module comprising a data acquisition circuit in communication with a controller circuit, the data acquisition circuit being configured to receive signals corresponding to measurements of electrochemical analyses of the electrochemical sample.

In some embodiments, the first layer comprises glass or plastic.

In some embodiments, the microfluidic components comprise glass or plastic.

In some embodiments, the at least one sensor or electrode includes at least one of a pH sensor, a temperature sensor, a dissolved oxygen sensor, a $CO_2$ concentration sensor, hydrogen peroxide sensor, a salinity sensor, a humidity sensor, a pressure sensor, an ammonia sensor, a sugar sensor (e.g., glucose sensor, fructose sensor, lactate sensor), an amino acid sensor (e.g., glutamine sensor, glutamate sensor), a nucleic acid sensor, a nutrient sensor, or a combination thereof.

In some embodiments, the electrochemical sensing device further includes a pump, the pump being configured to apply the negative pressure, at the port, different from the culture container to cause the portion of the electrochemical sample to flow from the culture container through the first channel to the sample container.

In some embodiments, the culture container is configured as an incubation compartment for cell or tissue culturing.

In some embodiments, the electrochemical sensing device further includes a wireless communication module comprising a communication circuit and antenna in communication with a controller circuit, the communication circuit and antenna being configured transmit, to a central data processing system, data corresponding to the measurements of electrochemical analyses of the electrochemical sample.

In some embodiments, the electrochemical sensing device further includes a housing and the controller circuit, the housing being coupled to the one or more substrates.

In another aspect, a method is disclosed of detecting culture parameters, the method comprising providing an electrochemical sensing device comprising: one or more substrates joined to form a culture container configured to retain an electrochemical sample, the one or more substrates forming a bottom surface and a side wall surface for the culture container that terminates at a top to define the culture container; a sample container in operative connection with the culture container through a first channel defined in the one or more substrates, the one or more substrates forming a second bottom surface and a second side wall surface that terminates at a second top to define the sample container, wherein the first channel has a cross-sectional area at a first end that expands to form the sample container and has a cross-sectional area at a second end that expands to form the culture container; and a port in operative connection with the sample container through a second channel defined in the one or more substrates, wherein application of a negative pressure, at the port, different from the culture container causes a portion of the electrochemical sample to flow from the culture container through the first channel to the sample container. The method further includes culturing a cell, tissue, organ, or a combination thereof in the culture container; applying the negative pressure at the port to inject an electrochemical sample from the culture container to the sample container through the first channel to the sample container; and acquiring signals from at least one sensor or electrode located in proximity to, or in, the sample container, wherein the signals are subsequently analyzed to assess the culture parameters.

In some embodiments, the method further includes adding nutrients or test agents to the culture container through a second port at the top of the culture container.

In some embodiments, the method further includes

In some embodiments, the method further includes collecting the electrochemical sample from the sample container through a third port at the top of the sampling container; and returning the collected electrochemical sample to the culture container through a fourth port.

In some embodiments, the culture container is formed of glass or inert material relative to the cell, tissue, organ, nutrients, or test agent.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Figure 1A:
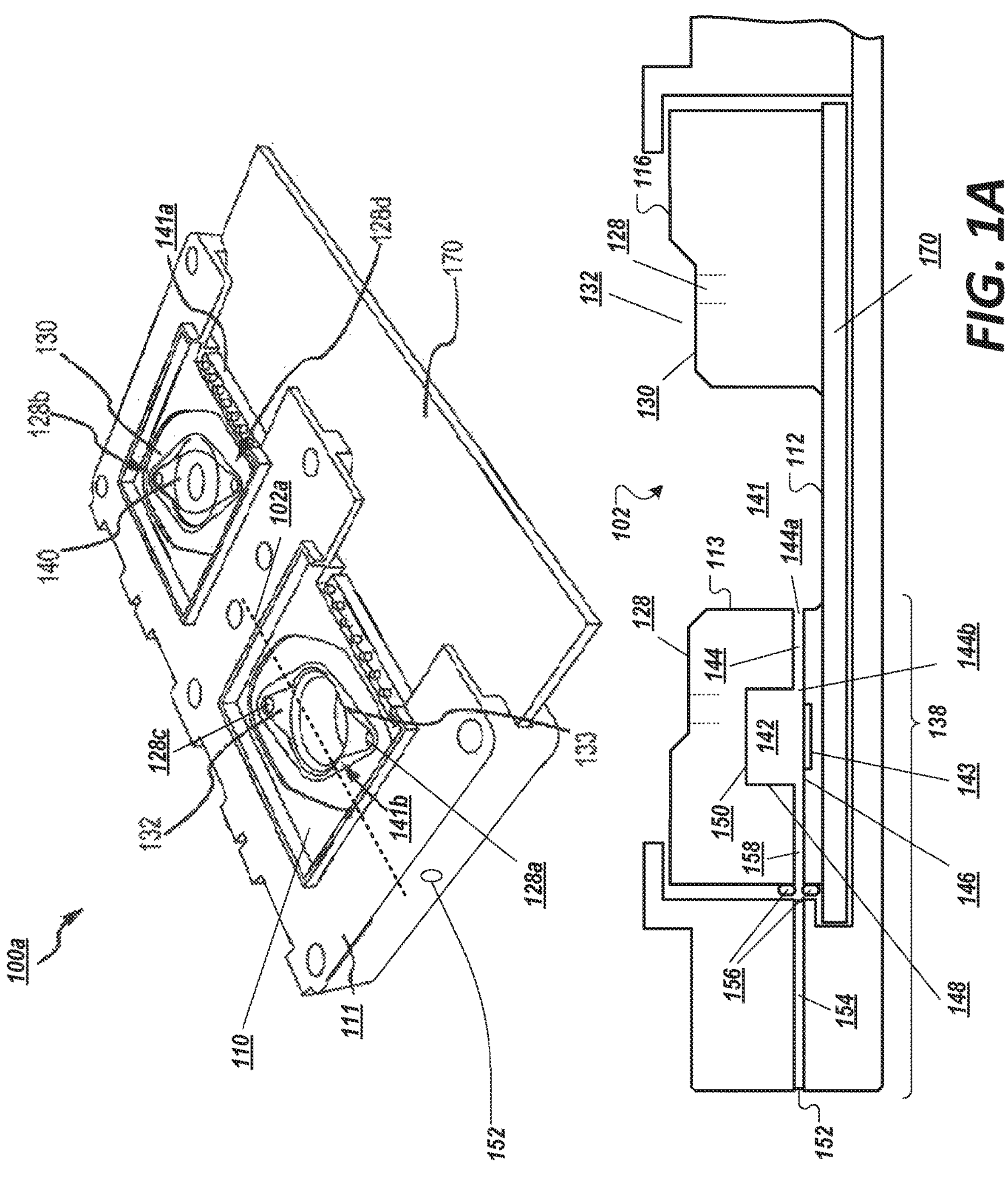
FIGS. 1A, 1B, 1C, and 1D, collectively, show an exemplary embodiment of the electrochemical sensing device configured as an Ussing chamber with a differential microvalve sampling assembly in accordance with an illustrative embodiment.

A number of embodiments of the disclosure have been described. Nevertheless, it will be understood that various modifications may be made without departing from the spirit and scope of the invention. Accordingly, other embodiments are within the scope of the following claims.

Definitions

To facilitate understanding of the disclosure set forth herein, a number of terms are defined below. Unless defined otherwise, all technical and scientific terms used herein generally have the same meaning as commonly understood by one of ordinary skill in the art to which this disclosure belongs. Publications cited herein and the materials for which they are cited are specifically incorporated by reference.

As used in this specification and the following claims, the terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. For example, the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof. Other than where noted, all numbers expressing quantities of ingredients, reaction conditions, geometries, dimensions, and so forth used in the specification and claims are to be understood at the very least and not as an attempt to limit the application of the doctrine of equivalents to the scope of the claims, to be construed in light of the number of significant digits and ordinary rounding approaches.

Accordingly, these terms are intended to not only cover the recited element(s) or step(s) but may also include other elements or steps not expressly recited. Furthermore, as used herein, the use of the terms "a," "an," and "the" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. A range may be construed to include the start and the end of the range. For example, a range of 10% to 20% (i.e., range of 10%-20%) can includes 10% and also includes 20%, and includes percentages in between 10% and 20%, unless explicitly stated otherwise herein.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein.

A "control" is an alternative sample used in an experiment for comparison purposes. A control can be "positive" or "negative."

Reference will now be made in detail to specific aspects of the disclosed materials, compounds, compositions, articles, and methods, examples of which are illustrated in the accompanying Examples and Figures.

Electrochemical Sensing Device and System #1

FIGS. 1A, 1B, 1C, and 1D show an exemplary embodiment of the electrochemical sensing device 100 (shown as 100*a*) configured as an Ussing chamber with differential microvalve sampling assembly in accordance with an illustrative embodiment. An Ussing chamber is an apparatus for measuring cell/tissue membrane properties (e.g., epithelial cells) in addition to detecting and quantifying transport and barrier functions of living tissue. In the example shown in FIGS. 1A-1D, the electrochemical sensing device 100*a* is configured to grow a cell or tissue culture and include embedded instrumentations to monitor the cell or tissue on an on-going basis.

Figure 1B:
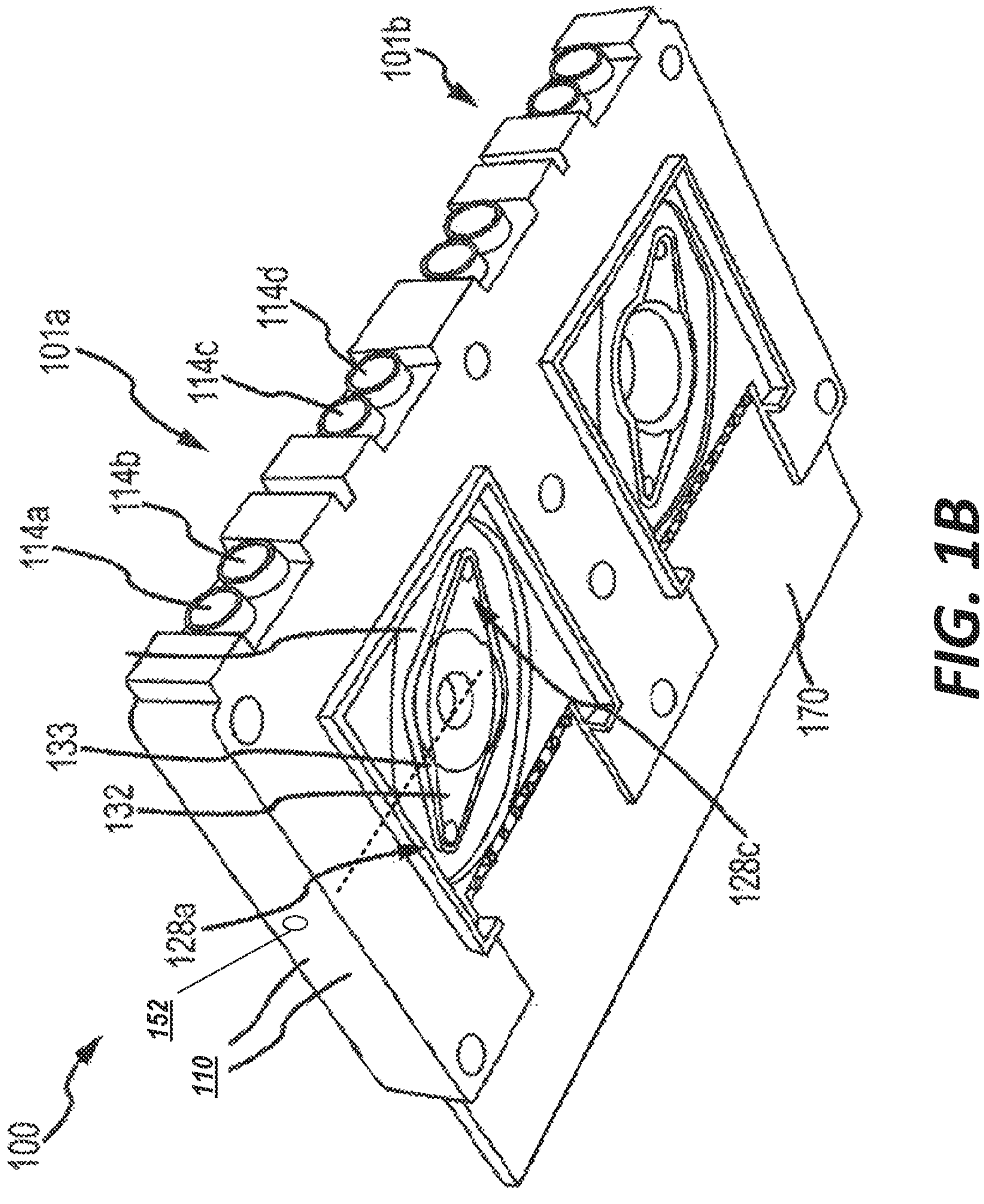

FIG. 1A shows a top, front, left-side perspective view of the electrochemical sensing device 100*a*. FIG. 1B shows a bottom, rear, right-side perspective view of the same electrochemical sensing device 100*a*. The electrochemical sensing device 100*a* (Ussing chamber device) includes a housing 110 configured to house an insert subassembly 140 mounted on a breakout board 170. The insert subassembly as a culturing container is configured to hold a cell or tissue (not shown), e.g., on an on-going basis, and an electrochemical sample to be analyzed. The housing 110 includes a plurality of fluidic or microfluidic channels to route fluids to the insert subassembly 140. An example channel may have a diameter of 2.5 mm or less, e.g., 2.2 mm or less.

FIG. 1A shows a cross-sectional view 102 of the electrochemical sensing device 100*a* at plane 102*a* over one of the insert subassemblies 140. The housing 110 of the electrochemical sensing device 100*a* is formed of one or more substrates joined to form the culture container 141 of the insert subassembly 140 is configured to slidably move into the housing 110. The one or more substrates of the housing 110 forms a bottom surface 112 and a side wall surface 113 for the culture container 141 that terminates at a top 116 to define the culture container 141. The top 116 of the culture container 141, in some embodiments, is configured to couple to a cover having one or more inlets that can couple to inlet tubings. In some embodiments, the cover may include an outlet for outlet tubings. The culture container 141 can be configured as an incubation compartment for cell or tissue culturing and may be formed of glass or inert material relative to the cell, tissue, organ, nutrients, or test agent.

The electrochemical sensing device 100*a* includes an integrated, separate sample container 142 (also referred to as a sampling container), as part of a differential micro-valve assembly 138, in operative connection with the culture container 141 through a first channel 144, e.g., a differential micro-valve, defined in the one or more substrates of the housing 110. The differential micro-valve assembly 138 is configured to perfuse, when desired via actuation, a small amount of solution volume from the culture container 141 into the sample container 142 that can then be monitored or analyzed for a target analyte or metric. The differential micro-valve assembly 138 is integrated with sensors 143 located within the sample container 142. Examples of sensor 143 can be an electrochemical sensor or electrode that is configured as a pH sensor, a temperature sensor, a dissolved oxygen sensor, a CO2 concentration sensor, hydrogen peroxide sensor, a salinity sensor, a humidity sensor, a pressure sensor, an ammonia sensor, a sugar sensor (e.g., glucose sensor, fructose sensor, lactate sensor), an amino acid sensor (e.g., glutamine sensor, glutamate sensor), a nucleic acid sensor, a nutrient sensor, or a combination thereof. To this end, the sensors 143 can be isolated from the cell or tissue culture and/or electrochemical sample until analysis of them are desired, and the sample is perfused into the sample container 142 with application of a negative pressure applied to port 152. The differential micro-valve assembly 138 includes channel 144, preferably, having micro-fluidic channel dimensions, and does not include any moving parts, making the assembly less prone to mechanical failure and more reliable at the micro-scale level.

In the example shown in FIG. 1A, the differential micro-valve assembly 138 is formed in the substrates of the housing 110, which form a second bottom surface 146 and a second side wall surface 148 that terminates at a second top 150 to define the sample container 142. The sample container is generally sealed. The first channel 144 has a cross-sectional area at a first end 144*a* that expands to form the sample container 142 and has a cross-sectional area at a second end 144*b* that expands to form the culture container 142.

The port 152 is in operative connection with the sample container 142 through a second channel 154 defined in the one or more substrates of the housing 110. The application of a negative pressure, at the port 152, different from the culture container 142 would cause a portion of the electrochemical sample to flow from the culture container 141 through the first channel 144 (differential micro-valve) to the sample container 142. The sample can be analyzed and then returned to the culture container 141 by application of a positive pressure that urges the portion of the electrochemical sample to flow from the sample container 142 through the first channel 144 (differential micro-valve) to the culture container 141. The electrochemical sensing device 100, via the differential microvalve operation, can do sampling for any number of times from the culture container 141 and return the sampled media to the culture container 141 after the analysis. In other embodiments, the sample can be removed from the sample container 142, via a removal port, and new media is added to the center chamber (i.e., 141).

In some embodiments, the port 152 is coupled to a pump configured to generate a negative pressure. The term "vacuum pump," as used herein, refers to a negative pressure generating pump that can provide a pressure less than atmospheric pressure. In other embodiments, the port 152 is coupled to a pressure source, valves, and actuators that can generate negative pressure at the port 152.

The automatic sampling operation using the differential micro-valve assembly 138 can replace or augment the pipetting operation of the sampled media from the culture container 141 for such measurements. The multiple repeated measurements via sensors in the differential micro-valve assembly 138 can be stored to generate a time-lapse data set of the media condition, including that of the oxygen consumption rate, and reactive oxygen species (ROS) production rate, among others described herein. The differential microvalves can provide both measurements for different analytes and their time-lapse information for each analyte measured.

In the example shown in FIG. 1A, the housing 110 of the culture container 141 is configured as an insertable board to a second housing 111. The second housing 110 can provide a framework for the attachment of glass covers and electronic boards as described in relation to FIG. 1C. To provide for an air-sealed connection between the port 152 located on the second housing 110 and the sample container 142 located in the housing 110, the housing 110 includes a gasket 156 to form the secure seal between the second channel 154 and the channel 158 connecting to the sample container 142. To prevent or reduce fluidic leakage through the differential micro-valve assembly 138 at the assembly's idle state, the channel 144 can be additionally adapted to include a thin flexible membrane, such as a rubber membrane (e.g., membrane with PDMS), that can form a flapped pin-hole (see FIG. 4). Such membrane can facilitate the control of the tightness of the differential micro-valve assembly for a given application.

Regarding the Ussing chamber operation, the housing 110 may be formed of two or more housing sections, each having the culturing container 141, e.g., fabricated of a polymeric material, such as PTFE or COC, e.g., via a molding process. In other embodiments (see FIG. 1B), the housing 110 may be formed of a single substrate. In the example shown in FIGS. 1A and 1B, the housing 110 is configured to partially form two chambers (shown as 141*a*, 141*b*), each configured to independently test two different culture samples simultaneously. The electrochemical sensing device 100*a* may be formed of any number of culture chambers, such as, for example, 1, 2, 3, 4, 6, 8, 10, 12, 16, 20, 24, 32, 48, 64, or 96 chambers.

Figure 1C:
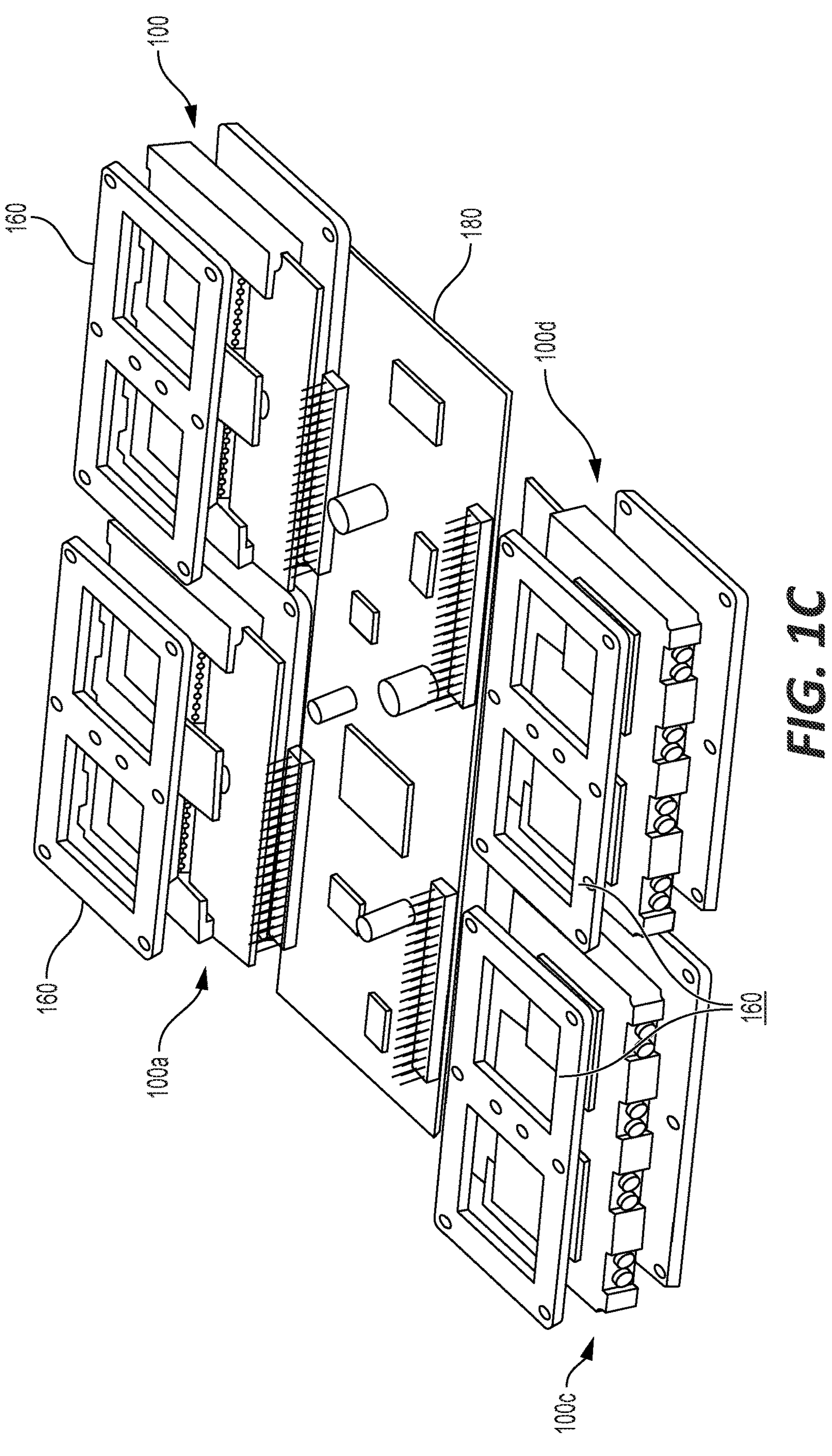
Figure 1D:
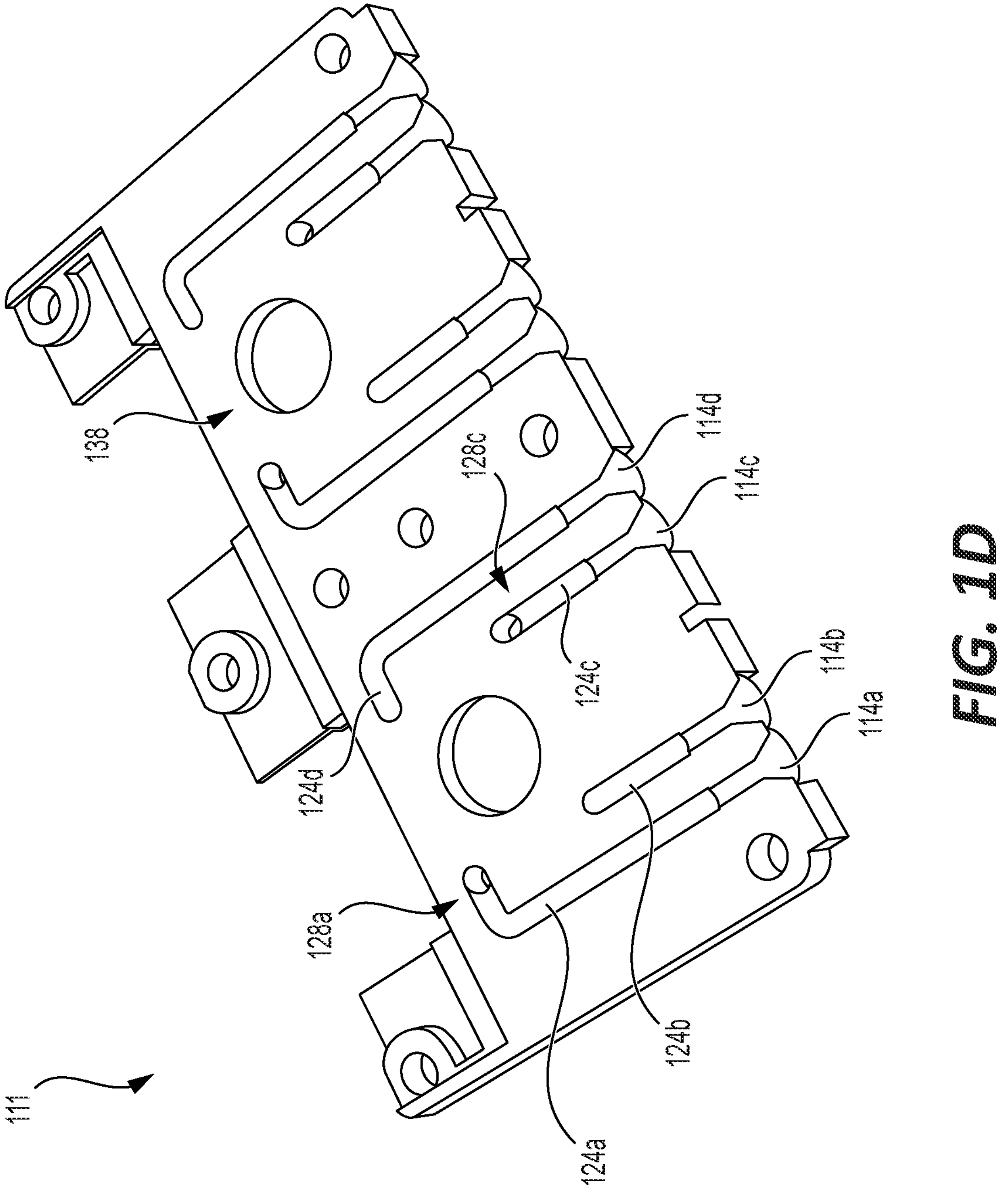

For the fluidic channels of the Ussing chamber, in FIG. 1B, an upper inlet port 114 (shown as 114*a*, 114*b*, 114*c*, 114*d*) is the starting point of the fluid pathway through the housing 111 that opens at a respective upper outlet through hole 128 (shown as 128*a*, 128*b*, 128*c*, and 128*d*) in the lateral channel 132 on the upper or top surface of the chamber assembly 100. FIG. 1D shows a cut-away of the housing 111 to show the fluidic channels of the upper inlet channel (124*a*, 124*b*, 124*c*, 124*d*) that connects the upper inlet ports 114 and the upper outlet through hole (128*a*, 128*b*, 128*c*, 128*d*).

The lateral channel 132 (FIGS. 1A and 1B) may be partially defined by the lateral channel wall 133 and/or lateral channel sealing gasket (not shown) configured to be positioned in a gasket landing 130. The lateral channel sealing gasket can provide a vertical sealing surface between lateral channel wall 133 and the glass cover 160 (see FIG. 1C). The gasket landing 130 can provide a seating surface for the lateral channel sealing gasket to help keep it positioned properly.

Assembly. FIG. 1C shows an assembled view of the electrochemical sensing system comprising multiple devices 100 of FIGS. 1A and 1B. FIG. 1D shows an internal view of the electrochemical sensing device 100*a*. The breakout board 170 is configured with connecting electrodes to couple to a circuit board 180. In the example shown in FIG. 1C, the multiple electrochemical sensing device 100 (shown as 100*a*, 100*b*, 100*c*, 100*d*) are each mounted with a glass cover 160 and connected to the circuit board 180 to form a multi-device assembly.

Additional description of the Ussing chamber may be found in U.S. Patent Publication No. 2021/0318286A1, which is incorporated by reference herein in its entirety.

Electrochemical Sensing Device and System #2

Figures 2A, 2B, 2C:
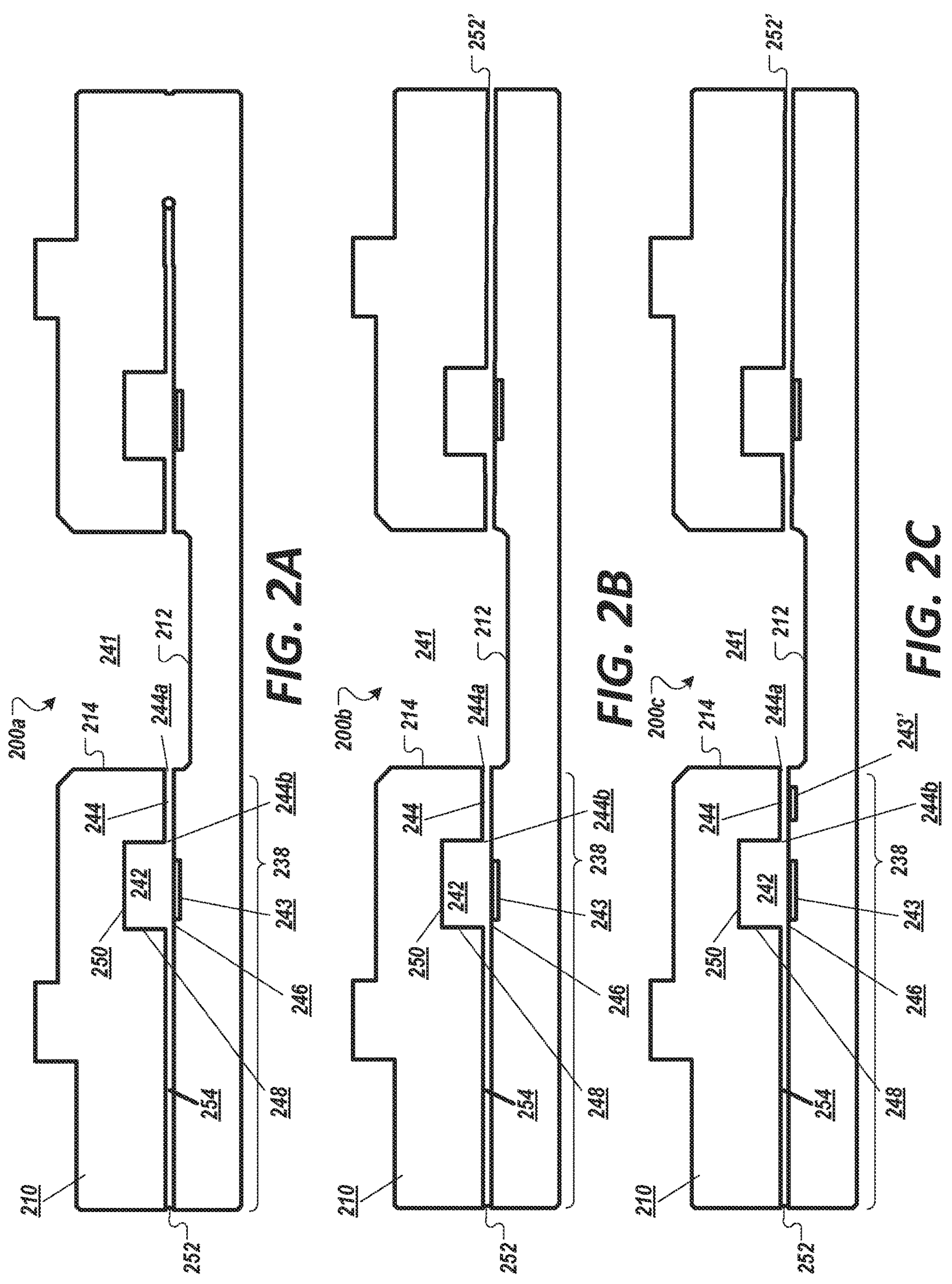
FIGS. 2A, 2B, and 2C each show another exemplary embodiment of the electrochemical sensing device configured as an Ussing chamber or other culturing chamber with the differential microvalve sampling assembly in accordance with an illustrative embodiment.

FIGS. 2A, 2B, and 2C each show another exemplary embodiment of the electrochemical sensing device 200 (shown as 200*a*, 200*b*, 200*c*, respectively) configured as an Ussing chamber or other culturing chamber with differential microvalve sampling assembly in accordance with an illustrative embodiment. In the example shown in FIGS. 2A-2B, the electrochemical sensing device 200*a*, 200*b*, or 200*c* is configured to grow a cell or tissue culture and include embedded instrumentations to monitor the cell or tissue in an on-going basis. FIG. 2A shows a side-view of the electrochemical sensing device 200*a*. FIG. 2B shows a side view of the electrochemical sensing device 200*b*. FIG. 2C shows a side view of the electrochemical sensing device 200*c*.

Similar to the device of FIGS. 1A-1D, the electrochemical sensing devices 200*a*, 200*b*, 200*c* also include a housing 110 (shown as 210) configured to house a culture container 141 (shown as 241). The culture container 241 is configured to hold a cell or tissue (not shown), e.g., on an on-going basis, and an electrochemical sample to be analyzed. The housing 210 includes a plurality of fluidic or microfluidic channels to route fluids to the culture container 241. FIG. 2A shows a configuration of the electrochemical sensing devices 200*a* with multiple culture containers 241 connected to a single port 152 (shown as 252), while FIG. 2B shows the electrochemical sensing devices 200*b* connected to its own respective port 152 (shown as 252 and 252').

The housing 210 of the electrochemical sensing device 100*a* is formed of one or more substrates joined to form the culture container 241. The one or more substrates of the housing 210 forms a bottom surface 212 and a side wall surface 214 for the culture container 241 that terminates at a top surface to define the culture container 241. The culture container 241 can be configured as an incubation compartment for cell or tissue culturing and may be formed of glass or inert material relative to the cell, tissue, organ, nutrients, or test agent.

The electrochemical sensing device 200*a*, 200, 200*c* includes an integrated, separate sample container 242, as part of a differential micro-valve assembly 238, in operative connection with the culture container 241 through a first channel 244 defined in the one or more substrates of the housing 210. The differential micro-valve assembly 238 is configured to perfuse, at the channel 244, when desired via controlled actuation, a solution volume from the culture container 241 into the sample container 242 that is instrumented with sensors to monitor or analyze for a target analyte or measure. The differential micro-valve assembly 238, in the example shown in FIGS. 2A-2C includes integrated sensors 243 located within the sample container 242. Examples of sensor 243 can be an electrochemical sensor or electrode that is configured as a pH sensor, a temperature sensor, a dissolved oxygen sensor, a $CO_2$ concentration sensor, hydrogen peroxide sensor, a salinity sensor, a humidity sensor, a pressure sensor, an ammonia sensor, a sugar sensor (e.g., glucose sensor, fructose sensor, lactate sensor), an amino acid sensor (e.g., glutamine sensor, glutamate sensor), a nucleic acid sensor, a nutrient sensor, or a combination thereof. FIG. 2C further shows additional sensors 243 (shown as 243') located in the channel 244.

The differential micro-valve assembly 238 terminates at a port 252 that is in operative connection with the sample container 242 through a second channel 254 defined in the one or more substrates of the housing 210. The application of a negative pressure, at the port 252, different from the culture container 241 would cause a portion of the sample volume (e.g., electrochemical sample) to flow from the culture container 241 through the first channel 244 to the sample container 242. The sample can be analyzed and then returned to the culture container 241 by application of a positive pressure that urges the portion of the electrochemical sample to flow from the sample container 142 through the first channel 144 to the culture container 241. The electrochemical sensing device 200*a*, 200*b*, 200*c*, via the differential microvalve operation, can do sampling for any number of times from the culture container 241 and return the sampled media to the culture container 241 after the analysis. In other embodiments, the sample can be removed from the sample container 242, via a removal port, and new media is added to the center chamber (i.e., 241).

Electrochemical Sensing Device and System #3

Figure 3A:
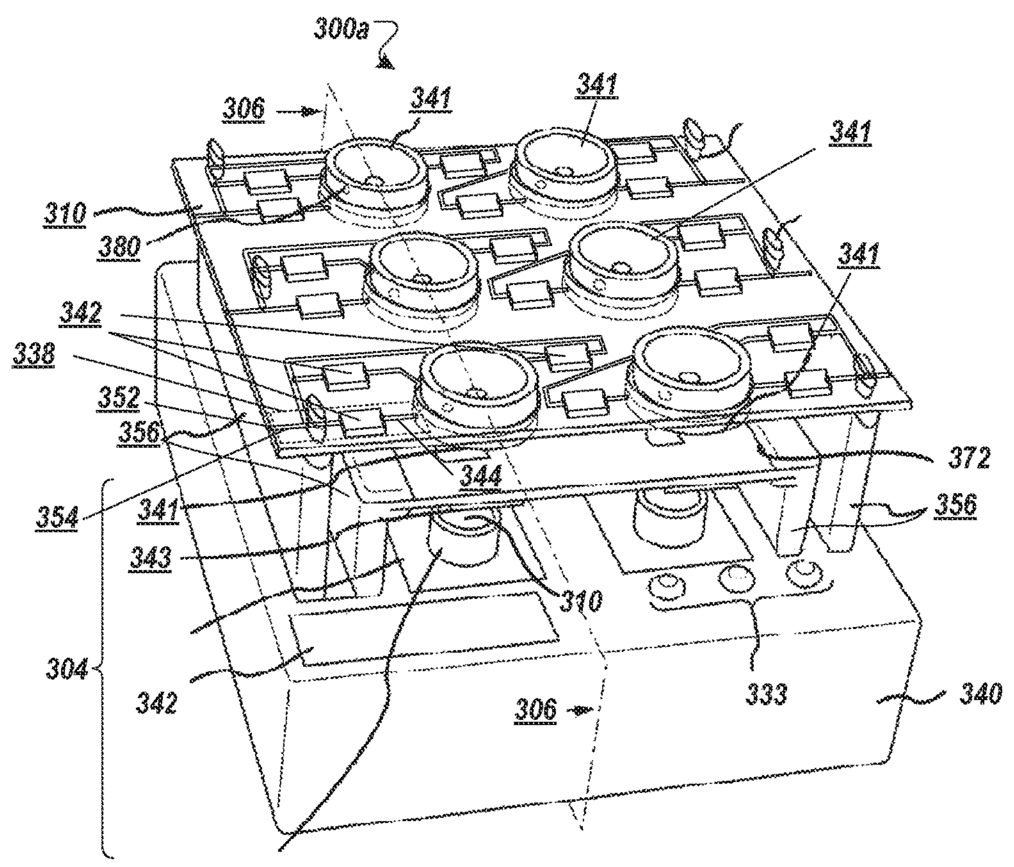
FIGS. 3A and 3B, collectively, show another exemplary embodiment of the electrochemical sensing device configured as a sensor-integrated well plate with the differential microvalve analyst sampling assembly in accordance with an illustrative embodiment.
Figure 3B:
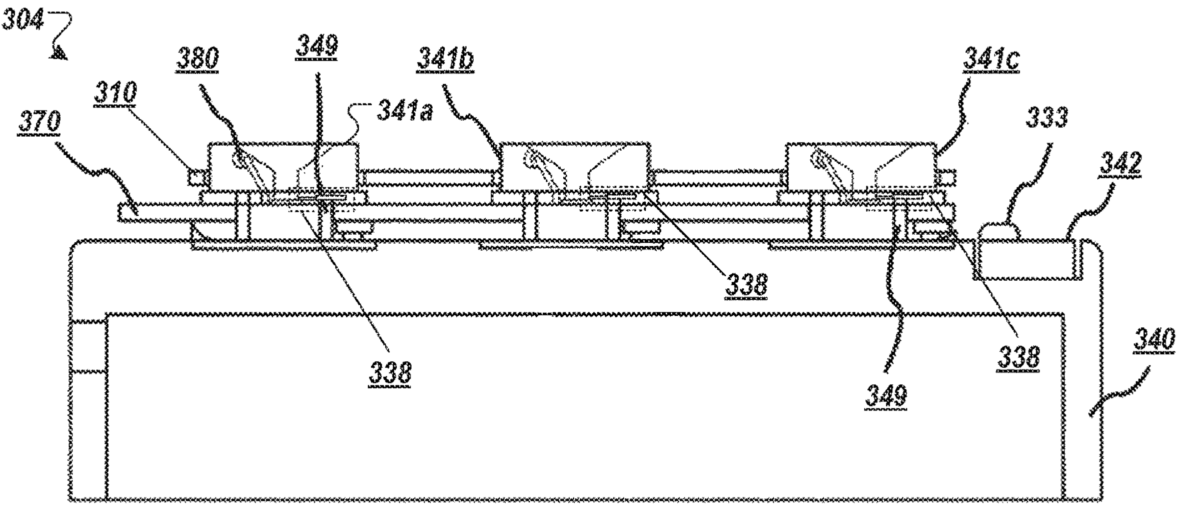

FIGS. 3A and 3B, collectively, show another exemplary embodiment of the electrochemical sensing device 300 (shown as 300*a*) configured as a sensor-integrated well plate with differential microvalve sampling assembly in accordance with an illustrative embodiment. In the example shown in FIG. 3A, the electrochemical sensing device 300*a* is configured to grow a cell or tissue culture and include embedded instrumentations 304 to monitor the cell or tissue on an on-going basis.

Similar to the device of FIGS. 1A-1D and FIGS. 2A-2C, the electrochemical sensing device 300*a* also includes a housing 110 (shown as 310) configured to house a culture container 141 (shown as 341). The culture container 341 is configured to hold a cell or tissue (not shown), e.g., on an on-going basis, and an electrochemical sample to be analyzed. FIG. 3A shows a perspective view of the electrochemical sensing device 300*a* over a set of culture containers 341. FIG. 3BA shows a cross-sectional view 304 of the electrochemical sensing device 300*a* at plane 306.

The housing 310 includes a plurality of fluidic or microfluidic channels to route fluids to the culture container 341. The housing 310 is formed of one or more substrates joined to form the culture container 341. The one or more substrates of the housing 310 forms a bottom surface and a side wall surface for the culture container 341 that terminates at a top surface to define the culture container 341. The culture container 341 can be configured as an incubation compartment for cell or tissue culturing and may be formed of glass or inert material relative to the cell, tissue, organ, nutrients, or test agent. The sidewall of the culture container 341 may include one or more connection ports 180 for connecting tubing (not shown) to which nutrients and/or test reagents may be directed into the culture container 341.

The electrochemical sensing device 300*a* includes an integrated, separate sample container 342, as part of a differential micro-valve assembly 338, in operative connection with the culture container 341 through a first channel 344 defined in the one or more substrates of the housing 310. In the example shown in FIGS. 3A and 3B, the housing 310 forms 12 differential micro-valve assemblies 338, a set of three for each of the culture container 341. The set of differential micro-valve assemblies 338 for each of the culture container 341 is connected to a respective first channel 344 that connects to the culture container 341. The set of differential micro-valve assemblies 338 for each of the culture container 341 are connected by microfluidic channels and terminates at a single port 352.

The differential micro-valve assembly 338 is configured to perfuse, at the channel 344, when desired via controlled actuation, a solution volume from the culture container 341 into the sample container 342 that is instrumented with sensors to monitor or analyze for a target analyte or measure. The differential micro-valve assembly 338, in the example shown in FIGS. 3A-3B includes integrated sensors (e.g., electrochemical sensor or electrode described herein) located within the sample container 342. Additional sensors may be located in the channel 344.

The application of a negative pressure, at the port 352, different from the culture container 341 would cause a portion of the sample volume (e.g., electrochemical sample) to flow from the culture container 341 through the first channel 344 to the sample container 342. The sample can be analyzed and then returned to the culture container 341 by application of a positive pressure that urges the portion of the electrochemical sample to flow from the sample container 342 through the first channel 344 to the culture container 341. The electrochemical sensing device 300*a*, via the differential microvalve operation, can do sampling for any number of times from the culture container 341 and return the sampled media to the culture container 341 after the analysis. In other embodiments, the sample can be removed from the sample container 342, via a removal port, and new media is added to the center chamber (i.e., 341).

Integrated System. In the example of FIGS. 3A and 3B, the electrochemical sensing device 300*a* is configured as an integrated sensor-well plate that interfaces with embedded instrumentations 304 comprising a processing unit board 370 and a connector board 372 to form an integrated sensor-well plate system. In the example, the integrated sensor-well plate and connector board 372 are each mounted to the processing unit board 370 across a respective arm connector 356. The connector board 372 may include interfaces to the electrodes and connects the electrochemical sensing device 300*a* to the processing unit board 370. In some embodiments, the connector board 372 includes a thermal unit and/or a motor unit.

The processing unit board 370, as a printed circuit board, includes a processing unit to control the operation of the electrochemical sensing device 300*a*. The processing unit board 370 may include front-end circuitries to condition, filter, amplifier, convert, and/or multiplex the acquired signal as well as digital components to store the acquired measurements and provide them to an external computing device for analysis (e.g., a central data processing system). The processing unit board may include a wireless communication module or component comprising communication circuitries and an antenna in communication to transmit the acquired measurement to the external computing device.

The processing unit board 370 may include a display 342, such as, for example, an LED display or LCD, connected to the processing unit and configured to display the status of the integrated sensor-well plate (also referred to as a smart well plate).

The instrumentation housing 340 may also include one or more input buttons 333 for inputting a command to the processing unit. The printed circuit board may include repeating patterns of through-holes 349 to connect to sensors (e.g., 243) located on the integrated sensor-well plate (e.g., 300*a*). The through-holes 349 may be circular having a diameter larger than the sidewalls of the culture container 341. The number of through-holes 248 may be equal to the number of culture containers 341. Suitable culture containers may include but are not limited to, for example, well plates (e.g., a single well, 6 wells, 12 wells, 24, wells, 48, wells, 96 wells, or any desired integer number of well plates).

The electrochemical sensing device 300*a* may be fabricated of a microfluidic board portion (e.g., made of glass or plastic, e.g., polymethyl methacrylate and includes the repeating pattern of culture containers 341) and a sensor board portion, e.g., a second plate (e.g., made of glass or plastic, e.g., polymethyl methacrylate that is fabricated with electrodes or sensors).

The sensor board portion may include conductive trace made, e.g., of carbon fiber, gold, silver, silver/silver chloride, platinum, or indium tin oxide (ITO). ITO may be used as a pH sensitive electrode. The conductive traces may further include surface coatings to enhance selectivity to various analytes, e.g., solid-state electrolyte such as Nafion and/or membrane for enhanced sensitivity to oxygen; glucose oxidase enzyme (GOx) and Nafion for enhanced sensitivity to glucose; and lactose oxidase (LOx) and Nafian for enhanced sensitivity to lactose; among other enzymes.

Additional description of the integrated sensor-well plate system and components may be found in U.S. Patent Publication No. 2020/0324289A1, which is incorporated by reference herein in its entirety.

Additional Example Systems

In yet another example, the culture container (e.g., 141, 241, 341, etc.) may be formed and located on one system and the sample container (e.g., 142, 242, 342, etc.) may be formed and located on a separate system that are connected by tubing.

Figures 5A, 5B, 5C, 5D:
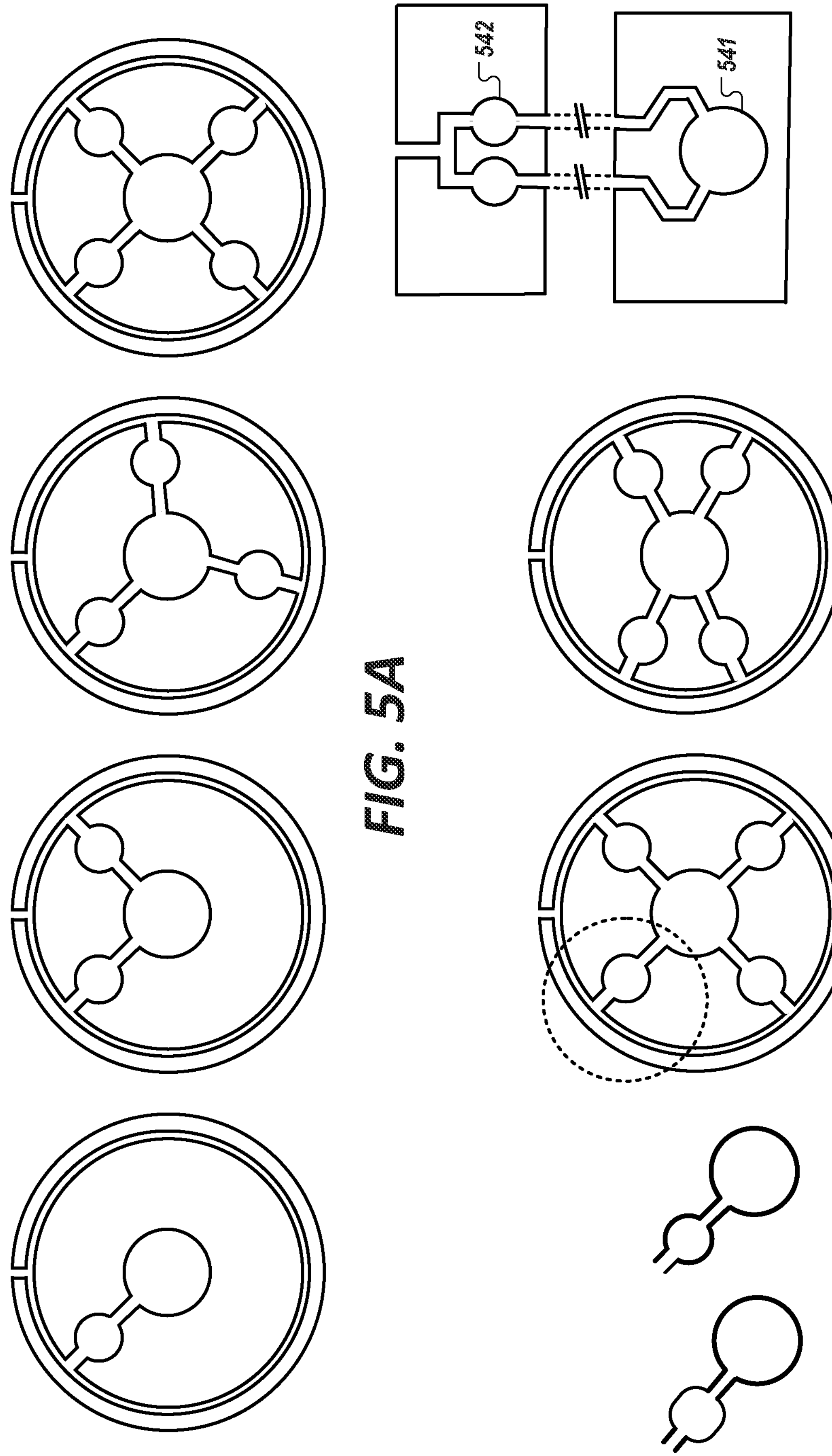
FIGS. 5A, 5B, 5C, and 5D show additional examples of configurations of the differential micro-valve assembly.

FIG. 5D shows an example of this configuration. In the example shown in FIG. 5D, the culture container (shown as 541) configured to grow a tissue or cell culture as described herein is located on a first device and is connected via tubing to two sample containers (542) located on a second device. The sample containers forms a part of a differential micro-valve assembly and can operate via actuation of a differential negative pressure as described in relation to FIGS. 1-3.

The connecting microfluidic channels of the respective devices and the tubing should define a similar, or same, volume between the two containers (541, 542) to ensure simultaneous filling and/or emptying.

Figure 3C:
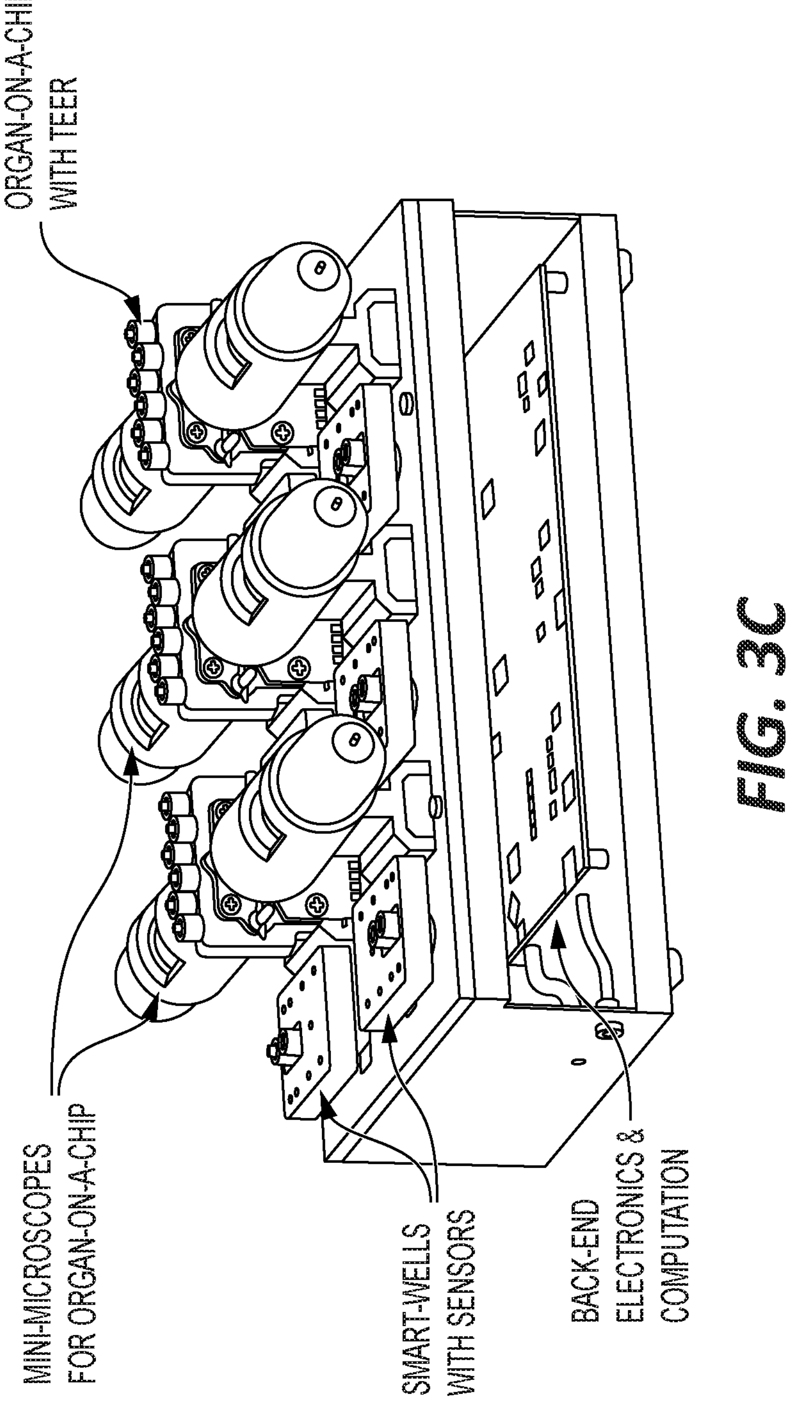
FIG. 3C shows the electrochemical sensing device configured with mini-microscopes.

In some embodiment, the Ussing chamber (for cell culturing and etc.) can be coupled with a closed smart-well system (for measurement). In other embodiments, a smart-well system (for cell culturing and etc.) can be coupled to another set of smart well system (for measurement). FIG. 3C shows an example implementation of this configuration. In FIG. 3C, the organ-on-chip (e.g., a Ussing chamber, a smart-well device, or other electrochemical sensing device as described herein) is fluidically coupled to a set of one or more smart well devices, each configured with sensors. To this end, the outlets of the device with the culture container (e.g., 141, 241, 341, etc.) is coupled to the respective inlet of the device with the sample container (e.g., 142, 242, 342).

Microscope Configuration. FIG. 3C also shows the electrochemical sensing device (shown as an organ-on-a-chip) configured with mini-microscopes. Specifically, the mini-microscopes is mounted to the side of the electrochemical sensing device to provide viewing of the samples in the culture container located in the electrochemical sensing device as an organ-on-a-chip device.

Example Differential Micro-Valve

Figure 4:
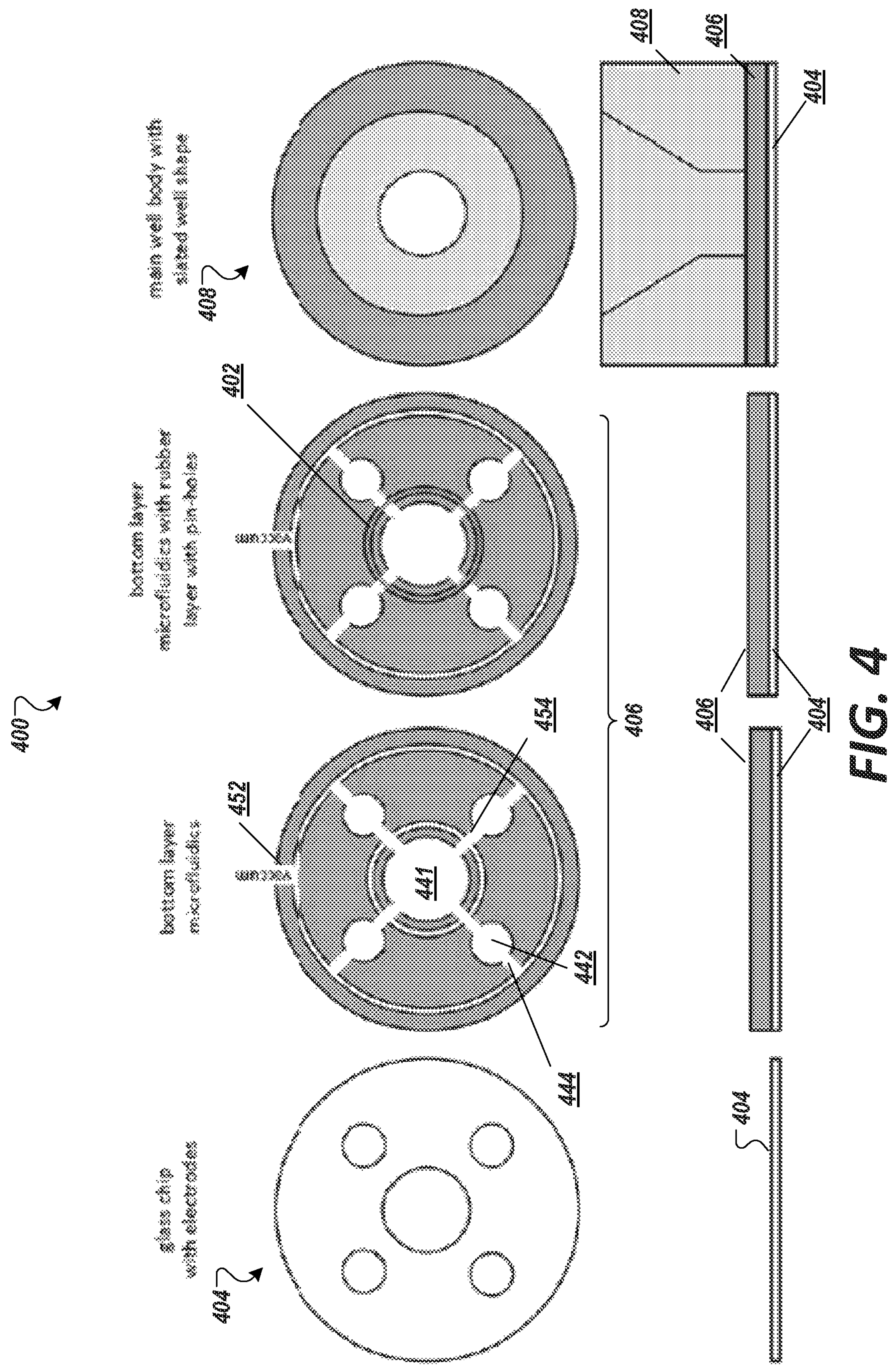
FIG. 4 shows an exemplary differential micro-valve assembly that can be employed to allow the movement of fluid within a controlled environment.

FIG. 4 shows an exemplary differential micro-valve assembly 400 (e.g., 138, 238, 338, etc.) that can be employed to allow movement of fluid within a controlled environment (e.g., in the system of FIGS. 1A-1D, 2A-2C, and 3A-3B). As described above, the differential micro-valve assembly 400 can be employed in a smart well plate (e.g., described in reference [28]) or other electrochemical sensing device described herein to dispense solution volume from each well for monitoring target analytes. While pipetting is common, it can be tedious and prone to error. The differential micro-valve assembly 400 can be integrated into a smart well plate or other electrochemical sensing device and is equipped with sensors located within each sampling well to provide a high-throughput smart well plate platform with a high degree of automation, e.g., in diagnostics and drug discovery applications.

The differential micro-valve assembly 400 can be characterized as mimicking the mechanism and functionality of individual droplet movement achievable using digital microfluidics technology, but without the associated technical challenges with the digital microfluidics, which can limit the applicability to a narrow range of fluid types, limit the reliability of fluid movement, and add design complexity. The differential micro-valve assembly can provide high reliability with a wide range of fluid types. Compared to conventional microvalve designs, the differential micro-valve assembly does not include moving parts in the valve to improve reliability, simplicity, and scalability.

The differential micro-valve assembly 400 can be implemented in an electrochemical sensing device that can operate on a variety of fluidic viscosities and the valve response time. The design parameters for the differential micro-fluidic may be dominated by the channel dimensions. The fluidic leakage through the differential micro-valve at the valve idle state can be controlled by employing thin flexible membranes 402, such as rubber membrane (e.g., membrane with PDMS), to form flapped pin-holes in, or in combination with, the differential micro-valve assembly. The flexible membrane 400 can adjust the tightness or flow resistance of the micro-valve for a variety of applications based on a tradeoff between cost and the valve leakage requirement.

The differential micro-valve assembly 400 can be implemented to provide a volume dispensed that is fixed using a discrete action by a vacuum pump or pressure differential generating pump. The differential micro-valve assembly is scalable to allow multiple assembly micro-valves to operate simultaneously from a single negative pressure source. Of course, additional pumps, pressure sources, valves, and actuators can be added to provide finer control if desired. Indeed, various modifications and additions can be made to the exemplary embodiments discussed herein without departing from the scope of the disclosed subject matter.

In the example shown in FIG. 4, the differential micro-valve assembly 400 may be formed from multiple substrate components that are attached to one another. The substrate components also include the microfluidic features as described herein, such as the culture container and associated microfluid channels. In the example, the multiple substrate components include a sensor substrate 404, a microfluidic substrate 406, and a well substrate 408.

The sensor substrate 404 can be formed of a glass chip and equipped with electrodes or sensors (e.g., 143, 243, 343, 343'). The sensors may include the electrochemical sensor or electrode described herein.

The microfluidic substrate 406 can form a bottom layer of the differential micro-valve assembly and includes microfluidic channels (e.g., 144, 244, 344, shown as 444 and 154, 254, shown as 454), sampling containers (e.g., 142, 242, 342, shown as 442), and the culture container (e.g., 141, 241, 341, shown as 441). The microfluidic substrate 406 also includes microfluidic channels that connect the multiple sampling containers 442 to the port (e.g., 152, 252, 352, shown as 452).

The well substrate 408 forms the main body of the culture container 441.

FIGS. 5A, 5B, 5C, and 5D show additional examples of configurations of the differential micro-valve assembly. In FIG. 5A, the electrochemical sensing device can be configured with any number of differential micro-valve assemblies, such as 1, 2, 3, 4, 5, 6, 7, 8, 9, 10.

FIG. 5B shows additional example geometric configurations of the differential micro-valve assembly. In FIG. 5B, the differential micro-valve assembly includes a circular chamber as well as an elongated circular chamber. Other geometries may be employed, including those described herein in FIGS. 1A-1D, 2A-2C, and 3A-3C. In FIG. 5A-5B, the differential micro-valve assemblies are symmetrically arranged. In other embodiments, e.g., FIG. 5C and FIG. 3A, the arrangement are not symmetrical. FIG. 5D shows the differential micro-valve assembly (having the sample container) connected to the culture container over tubings to provide measurement operation of the culture container.

Example Methods of Operation

Figure 6:
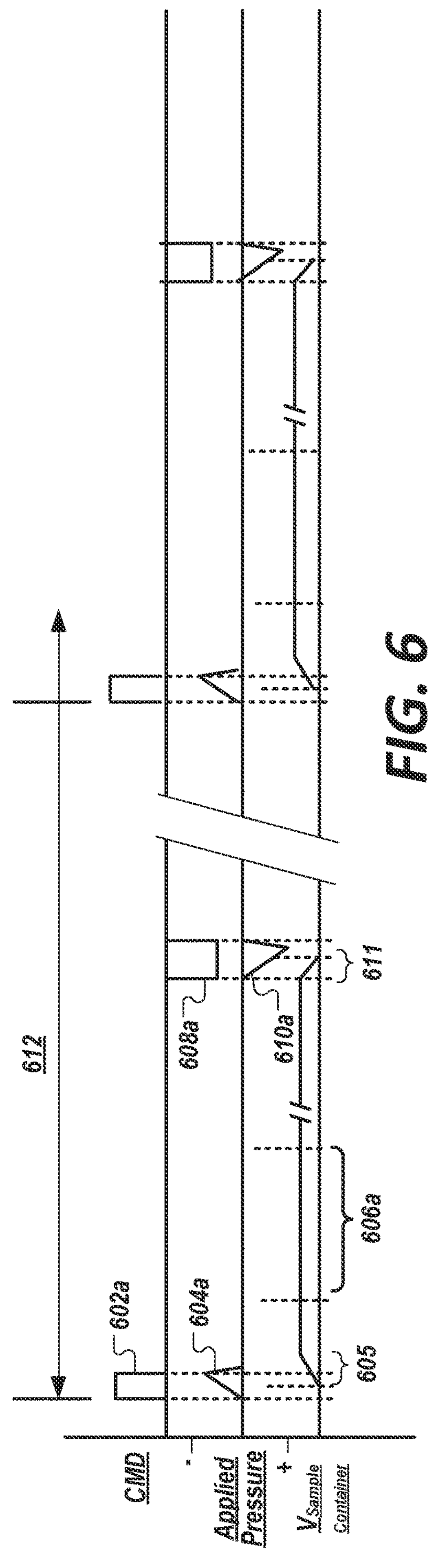
FIG. 6 is a diagram showing an example method of operation for the electrochemical sensing devices and differential micro-valve, e.g., of a system described in relation to FIGS. 1A-1D, 2A-2C, and/or 3A-3C.

FIG. 6 is a diagram 600 showing an example method of operation for the electrochemical sensing devices and differential micro-valve, e.g., of a system described in relation to FIGS. 1A-1D, 2A-2C, and/or 3A-3C. In the example shown in FIG. 6, a controller (e.g., 370 or other processing units disclosed herein) is configured to generate a command 602 (shown as 602*a*) to initiate an analysis sequence of one or more analysts in a culture container (e.g., 141, 241, 341, etc.) having contained within a cell or tissue culture. The cell or tissue culture can be monitored and grown, typically independent of the sampling process. In some embodiments, the analysis via the sampling operation can be performed in synchronicity with the operation associated with the cell or tissue culture, e.g., a pre-defined after additional nutrients or test agent is introduced into the culture container.

In this example, based on the duration of the command 602*a*, a negative pressure (shown as applied pressure 604 (shown as 604*a*) is applied to the port (e.g., 152, 252, 352, 452, etc.) of the differential micro-valve assembly (e.g., 138, 238, 338, 438, etc.). With the application of the negative pressure at the port of the differential micro-valve assembly (e.g., 138, 238, 338, etc.), a controlled sample volume is directed (605) from the culture container (e.g., 141, 241, 351, 451, etc.) through channel 144 (or 244, 344, 444, etc.) to the sample container (e.g., 142, 242, 342, 442). The sample container (e.g., 142, etc.) may be instrumented with sensors (e.g., 143, 243, 243', 343, 443, etc.) that can take a measurement 606 (shown as 606*a*) of the sample volume and provide the measurement to the controller (e.g., 370). In other examples, the command may be a time value to be utilized by a pump controller to control the actuation of a pump. In yet other embodiments, the command can be used to actuate a valve for a pre-defined period of the command. Subsequent to the measurement 606*a*, the controller (e.g., 370, etc.) is configured to generate a command 608 (shown as 608*a*) to return the sample volume in the sample container (e.g., 142, etc.) back to the culture container (e.g., 141, etc.). The command 608*a* directs the application of a positive pressure (shown as applied pressure 604 (shown as 604*a*) to be applied to the port (e.g., 152, 252, 352, etc.) of the differential micro-valve assembly (e.g., 138, 238, 338, etc.) which then urge (611) the sample volume in the sample container (e.g., 142, etc.) back to the culture container (e.g., 141, etc.). In other embodiments, other mechanisms may be employed to clear the sample volume from the sample container (e.g., 142, etc.), e.g., directing to a waste bin. Multiple repeated measurements via sensors in the sample container can be stored to generate a time-lapse data set of the sample volume, e.g., oxygen consumption rate, ROS production rate, among others described herein. The controller (e.g., 370) is configured via pre-defined time or trigger conditions, e.g., via instructions, to repeat the measurement (see 612).

EXPERIMENTAL RESULTS AND ADDITIONAL EXAMPLES

By way of non-limiting illustration, examples of certain embodiments of the present disclosure are given below.

Experimental Study

A study was conducted employing metabolic multi-sensors that enable an integration of bioenergetic assessments from a single sample, which has the potential to advance clinical and scientific research into immunologic and infectious diseases, cancer, and cardiometabolic disorders. The device in the study facilitated the simultaneous measurement of consumption rate (OCR) and hydrogen production rate (HPR) that can provide an opportunity to monitor relative shifts in metabolic flux and reactive oxygen species (ROS) production from very small biological samples. The technology is compatible with existing micro-metabolic multi-sensor platforms. However, the close proximity of sensors is prone to sensor-sensor interference, especially when sensors using similar enzymatic mechanisms, such as using glucose oxidase for glucose sensor and lactate oxidase for lactate sensor, respectively.

The method employed in the study subtracted the baseline amperometric current from current measurements when mitochondria were present may be sufficient for $O_2$ and $H_2O_2$ measurements, fully integrating the present device with those having other sensor types, such as glucose and lactate sensors, will require additional design considerations to minimize the impact of sensor-sensor interferences. In an alternative embodiment, a device design incorporating changes can minimize sensor-sensor interferences to allow for simultaneous measurements of more metabolites. It can be used to evaluate cellular metabolism and mitochondrial function in health and disease. The measurements can, for example, be acquired using the exemplary differential micro-valve assembly described herein.

Example 1: Analysis of Mitochondrial Oxygen Consumption and Hydrogen Peroxide Release from Cardiac Mitochondria Using Electrochemical Multi-Sensors Mitochondria are the primary sites of oxygen ($O_2$) consumption and energy metabolism in most cell types, but they also produce reactive oxygen species (ROS) that contribute to a wide array of pathological and physiological processes. Accordingly, simultaneous monitoring of mitochondrial ROS release and oxygen consumption rate (OCR) from cells and mitochondrial preparations is an attractive investigative approach in biological research, particularly when sample quantity is scarce. This paper presents the development of a sensitive multi-sensor device capable of measuring ROS production and OCR from biological samples in a single micro-chamber assay. Sensor sensitivities for $O_2$ and hydrogen peroxide ($H_2O_2$; the major ROS species released by mitochondria and cells) are 4.32 nA/μM and 54.89 nA/μM, respectively, with limits of detection of 2.9 μM and 58.36 nM, respectively. Proof-of-concept studies in isolated mitochondria from rat cardiac tissue (5 μg protein) demonstrate an expected 3-4 fold increase in $H_2O_2$ release over the basal rate following the addition of respiratory substrates, with a comparatively small change in OCR. The subsequent addition of adenosine diphosphate (ADP) decreased $H_2O_2$ release by 73% ($p<0.01$) and increased OCR by 168% ($p<0.01$), consistent with established shifts in mitochondrial membrane potential and electron flow from an ADP-limited (State 4) to ADP-stimulated (State 3) respiratory state. These studies validate the results from the use of a novel multi-sensor device capable of monitoring OCR and $H_2O_2$ simultaneously in scarce biological samples, with potential utility in the non-destructive integrative study of cellular metabolism and mitochondrial function.

Background Mitochondrial respiration accounts for the majority of oxygen ($O_2$) consumed by living cells, serving as the final electron acceptor to produce water in the oxidative phosphorylation (OXPHOS) of adenosine diphosphate (ADP) to ATP. However, a small proportion of $O_2$ consumed by mitochondria is reduced by single electrons to produce superoxide radicals in the electron transport system [1]. These and other mitochondria-derived reactive oxygen species (ROS) play important roles in physiological cell signaling but have also been implicated in the development of diabetes [2], cardiovascular disease [3], and neurodegenerative disorders [4]. Most superoxide is rapidly converted to hydrogen peroxide ($H_2O_2$) in the mitochondrial matrix and inner membrane space, where it can readily cross mitochondrial membranes to damage cellular components and trigger cell signaling cascades [5]. The rates of mitochondrial $H_2O_2$ efflux are influenced by a complex interaction of intrinsic and extrinsic factors that vary substantially across cell types, respiratory states, and assay conditions, rather than being a fixed proportion of mitochondrial respiration [6, 1, 7].

Several methodologies have been developed for monitoring ROS release from various sample types in vitro [8], most commonly utilizing fluorophores such as Amplex® UltraRed to monitor changes in media $H_2O_2$ levels [6, 9]. These approaches are typically employed in isolated mitochondria in the absence of ADP (State 4 or "LEAK" respiration), where mitochondria are energized with substrates that maximize mitochondrial ROS production relative to the oxygen consumption rate (OCR) in order to generate the most robust signal [10]. However, the rate of $H_2O_2$ release is much lower during oxidative phosphorylation (State 3 or "OXPHOS-linked" respiration) when OCR is much higher, leading to shifts in the ratio of ROS production and OCR that provide important insight to mitochondrial responses to physiological and pathological stress. Commercial platforms relying on fluorescence intensity measurement, such as Seahorse XF or Synergy HTX, can provide information on mitochondrial oxidative stress via OCR and/or extracellular acidification rate (ECAR) to infer the level of ROS production. However, they do not directly measure ROS production, let alone providing simultaneous measurement of OCR and ROS production to gain better understanding of the relationship between OCR and ROS production under a variety of conditions. Increasing interest in the relationship between cellular ROS production and $O_2$ consumption rates under these dynamic conditions has led to new instrumentation and methodology for simultaneous monitoring of OCR and $H_2O_2$ release from various sample preparations [11, 6, 12]. However, these new techniques allowing simultaneous monitoring of OCR and $H_2O_2$ production also rely on fluorescence and requires large quantity of biological samples.

The aim of the study was to develop and test a metabolic microsensor technology capable of monitoring OCR and $H_2O_2$ release from small biological samples that could be easily integrated with existing multi-sensor platforms recently described in the literature [13, 14]. The sensor device presented in this paper performs simultaneous $O_2$ and $H_2O_2$ measurements electrochemically to allow miniaturization and monitoring results in real-time. The study designed and fabricated the first metabolic multi-sensor that combines electrochemical and potentiometric sensors capable of monitoring OCR, $H_2O_2$, and pH in the same sample microchamber. Given descriptions of the pH sensor in previous publications [14], the study demonstrated the performance and integration of the $O_2$ and $H_2O_2$ sensors utilizing isolated mitochondria at quantities <10% of those routinely used in existing commercial platforms [6, 12].

Materials and Methods

Sensor electrode design, fabrication, and surface modification. A multi-sensor chip was designed with a total of six sensors, five of which are electrochemical type sensors, and the sixth sensor is a potentiometric type sensor for pH measurement. One electrochemical sensor was designated for $O_2$ measurement and the other four were designated for $H_2O_2$ measurement. Each electrochemical sensor was designed in a three-electrode electrochemical cell configuration with a working electrode (WE), a reference electrode (RE), and a counter electrode (CE). The RE and CE are shared between $O_2$ and $H_2O_2$ sensors. Both the WEs and CEs are gold electrodes, and the REs are Ag/AgCl electrode.

Figures 7A, 7B, 7C, 8A, 8B, 8C, 9:
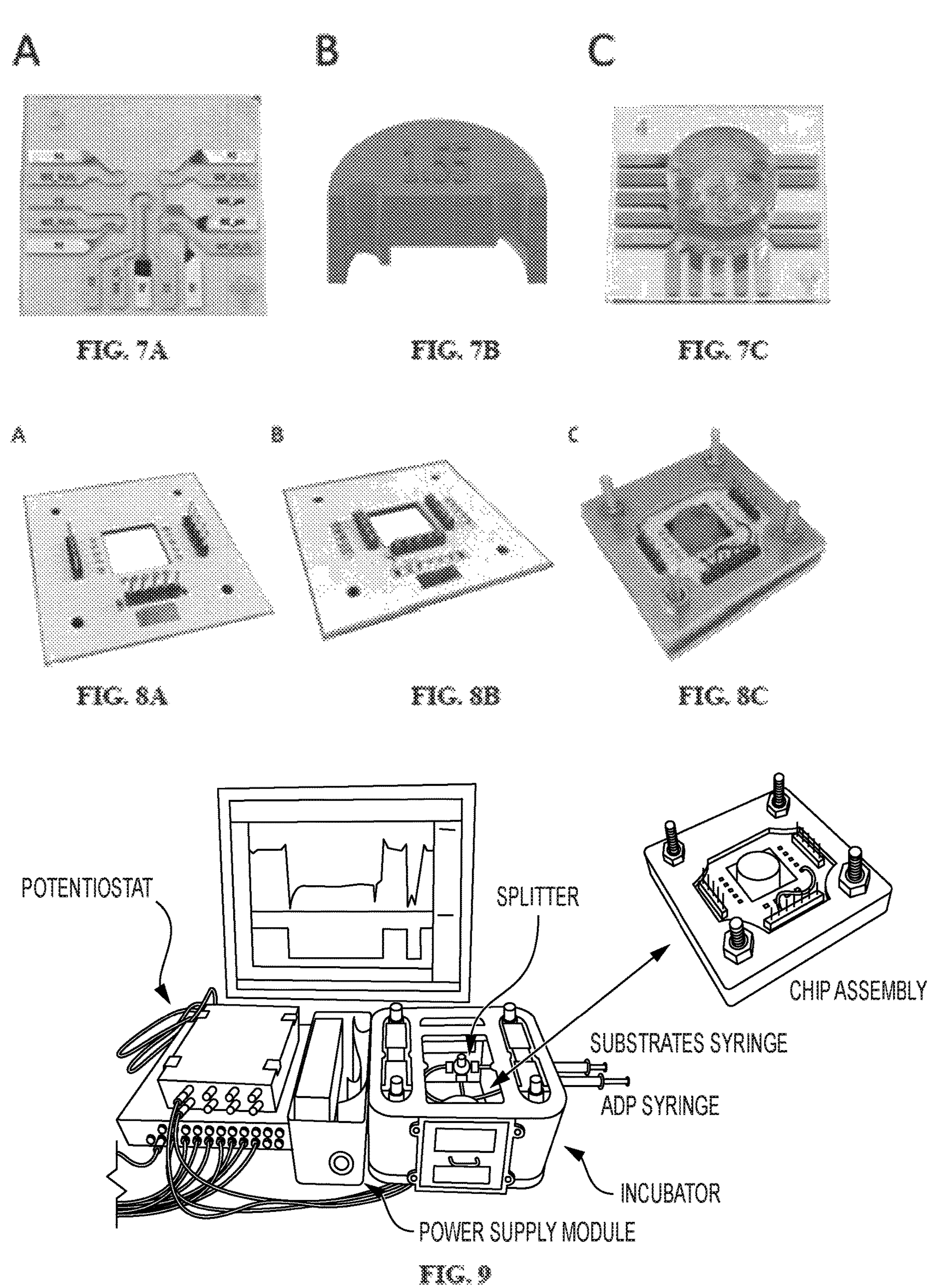
FIGS. 7A, 7B, 7C. (7A) Multi-sensor chip. CE is shared between the $O_2$ sensor and the $H_2O_2$ sensor. WE of the $O_2$ sensor and WE of the $H_2O_2$ sensor are labeled as WE_$O_2$ and WE $H_2O_2$, respectively, and all WE $H_2O_2$'s are shorted externally in order to have a larger WE area. All REs are also shorted externally except for RE_pH, which was not used in experiments described in this paper. An ITO-based WE of the pH sensor is labeled as WE_pH, which was not used in the experiments described in this paper either. (7B) Microchamber design with an inlet (left) and an outlet (right) on the top. (7C) Photo of an actual sensor chip with the microchamber mounted on it.
FIGS. 8A, 8B, 8C. (8A) and (8B) are the top and bottom sides of PCB, respectively, used for making connections between the glass sensor chip and the external potentiostat. (8C) Final assembly of the multi-sensor chip module.
FIG. 9. The setup of the measurement system consisting of a customized incubator, syringes for injecting therapeutics, a three-way splitter, the sensor chip assembly, and a potentiostat.

The multi-sensor chip was fabricated on a 25 mm×25 mm glass substrate through standard photolithography using S1813 positive photoresist (Megaposit, Dow, USA), the developer of S1813 (Megaposit MF-26A, Dow, USA), and thermal evaporation. Details of photolithography and thermal evaporation can be found in the previous project [13]. FIG. 7A shows a finished multi-sensor chip with each electrode labeled.

The $O_2$ sensor has a 1 mm diameter WE while the $H_2O_2$ sensor has four 1 mm diameter WE's in the four corners of the well electrically shorted to have a larger WE area. After rinsing the sensor surface with methanol and deionized (DI) water followed by 1% Triton X-100 (Sigma-Aldrich, USA) for 20 min, a solid electrolyte layer was formed on the WE surface of the $O_2$ sensor by drop coating 0.1 μl Nafion solution (5% w/w, Sigma-Aldrich, USA) as previously described [15]. The preparation of the WE of the $H_2O_2$ sensor was adapted from [16]. An electropolymerization charge of 35 mC $cm^{-2}$ was applied when polymerizing the electrode with a mixture of horseradish peroxide (Sig-ma-Aldrich, USA) and pyrrole (Sigma-Aldrich, USA) as conducting polymers. The silver/silver chloride (Ag/AgCl) pseudo-RE was prepared by oxidizing the silver electrodes with 50 mM ferric chloride for 20 min at room temperature. Finally, the sensor was rinsed with deionized water.

Microchamber design and fabrication. In the study, a microchamber well sits on the multi-sensor glass chip to house cells inside the microchamber during measurement. The microchamber well has an internal volume of 180 μl. FIG. 7B shows the cross-section of the microchamber well design. There is an inlet to the left and an outlet to the right of the well. The inlet has a slightly lower entry point inside the microchamber well to allow media or other therapeutics to reach the cells inside the well better. The tubing from the inlet was attached to a three-way splitter (not shown in FIG. 7A-7C) to allow two different therapeutics (i.e., respiration substrate and ADP) to be injected into the microchamber using two syringes. The microchamber well was printed using a stereolithography (SLA) 3D printer with a biocompatible resin (SG, NextDent, Netherlands). The well was then bound to the glass chip with double-sided tape (468MP, 3 M, USA) patterned by a laser cutter (LS1416, Boss Laser, USA). FIG. 7C shows the microchamber attached to the sensor chip glass substrate.

Printed circuit board and chip holder. In the study, the printed circuit board (PCB) was designed and manufactured to provide connections between electrodes on the multi-sensor glass chip and the external potentiostat. As shown in FIG. 8A, the PCB has a rectangular opening in the middle to accommodate the microchamber well on the multi-sensor glass chip. A set of spring-pin connectors whose pin pitch matches the pitch of the electrode pads at the edge of the multi-sensor glass chip are mounted at the edges of the rectangular opening of the PCB. After mounting the microchamber well on to the glass multi-sensor chip, the glass multi-sensor chip is slid into the PCB to allow the electrodes on the glass chip to make contacts to the PCB via the spring-pin connectors (see FIG. 8B). The connections were further secured by the use of two aluminum chip holder sandwiching the PCB and the multi-sensor glass chip in the middle with four screws to complete the final assembly. The pins of the spring-pin connectors on top of the board (shown in FIG. 8A) were then used for making connections to the external potentiostat (Quadstat EA164H, eDAQ, USA). FIG. 8C shows the final assembly of the multi-sensor chip module ready for measurement.

Mitochondrial isolation. In the study, cardiac mitochondria used were isolated from adult (4-5 month old) male Fischer 344 (CDF) rats obtained from Charles River (Wilmington, MA) housed in a temperature and humidity-controlled facility on a 12:12 h light:dark cycle and provided water and chow (Purina 2918) ad libitum. Animals were sacrificed for tissue collection by midline thoracotomy and removal of the heart following confirmation of deep anesthesia by sodium pentobarbital injection (100 mg/kg i.p.) using procedures approved by the Colorado State University Care and Use Committee and conform to the Guide for the Care and Use of Laboratory Animals published by the U.S. National Institutes of Health (NIH Publication No. 85-23, revised 1996).

Mitochondria were isolated from left ventricular cardiac tissues using standard differential centrifugation methods, essentially as previously described [17]. All procedures were performed on ice or controlled at 4° C. immediately upon harvesting fresh tissue. Hearts were excised and trimmed free of connective tissue, atria, and valves to pro-vide myocardial tissue, then rinsed and minced in ice-cold Chappell-Perry (CP1) buffer consisting of (in mM) 100 KCl, 50 MOPS, 1 EDTA, 5 EGTA, $5MgSO_4.7H_2O$, and 1 ATP, pH 7.4 with KOH. Minced tissue was then homogenized for 10 s at medium speed using a polytron and incubated in CP1 containing trypsin (~5 mg/g tissue) for 7 min to disrupt myofibrils in order to extract both interfibrillar and subsarcolemmal mitochondria. Trypsinized homogenates were then subjected to 6 passes with glass-Teflon Potter-Elvehjem homogenizer prior to centrifugation at 600×g. The supernatant (containing mitochondria) was collected and centrifuged at 7000×g to pellet mitochondria, followed by three 7000×g clarifying spins in CP1+2 mg/ml albumin, then once in stabilization buffer containing 100 mM KCl, 50 mM MOPS, 0.5 mM EGTA. Final mitochondrial pellets were resuspended in KME at a final protein concentration of ~5 μg/μl determined by the bicinchoic acid (BCA) assay (ThermoScientific).

Respiration buffers and stimuli for isolated mitochondria. Mitochondrial suspensions (5 μg protein) were added to the sensor microchamber containing 180 μl of mitochondrial respiration medium (MiR05) containing (in mM) 0.5 EGTA, $3MgCl_2$ hexahydrate, 60 lactobionic acid, 20 taurine, $10KH_2PO_4$, 20 HEPES, 110 sucrose, and 0.1% BSA, pH 7.1 with KOH, which was selected based on rigorous testing that determined this formulation to have the highest stability and sensitivity for simultaneous OCR and $H_2O_2$ measurements [18], and prior use in other metabolic multi-sensor platforms [13, 14]. For our proof-of-concept studies, we selected an experimental protocol used to evaluate the relationship between OCR and hydrogen peroxide pro-duction rate (HPR) by energized mitochondria during the metabolic shift from a high-membrane potential/low ATP demand (LEAK) state to a lower-membrane potential/high ATP demand (OXPHOS) state [6].

To account for potential interactions between the sensor and the mitochondrial respiration medium, baseline measurements were performed before each measurement without any mitochondria present at the sensor site and were subtracted from the $O_2$ and $H_2O_2$ measurements obtained with mitochondria present. Following a baseline stabilization period, mitochondria were energized with saturating concentrations of substrates that fully reconstitute forward flux of the citric acid cycle, supplying electrons to the mitochondrial respiratory chain through Complexes I and II (in mM): 1 malate, 5 pyruvate, 10 glutamate, and 20 succinate. Flux was then recorded until it stabilized to establish OCR and HPR under LEAK state conditions, after which time ADP (2.5 mM) was added to establish OCR and HPR in the OXPHOS state. With the in-situ baseline calibration method, the data presented were based on the net increase from $H_2O_2$ release from superoxide production inside mitochondria. Previous studies have described these potential interactions in other $H_2O_2$ assay platforms, correcting for them by similar calibration experiments [6].

Sensor activation voltages. Activation voltages used in amperometry for both $O_2$ and $H_2O_2$ measurement were obtained from cyclic voltammetry (CV) data with a scan rate of 100 mV/s. Four $O_2$ concentrations (100%, 70%, 35%, and 0%) were used with each concentration having 5 repeats. Samples were prepared by bubbling nitrogen gas to deionized water and the resulting $O_2$ concentration was confirmed by using a commercial oxygen meter (DO6 +, Oakton, USA). The CV curves for $H_2O_2$ sensor were obtained using solutions made with phosphate-buffered saline and $H_2O_2$ solution (Sigma-Aldrich, USA). The solutions were prepared by diluting a known $H_2O_2$ concentration solution to the concentrations needed for performing CV. A total of 5 concentrations (11 μM, 2.76 μM, 690 nM, 172.5 nM, 0 nM) were used for obtaining the activation voltage.

Oxygen sensor calibration. Using the activation voltage for $O_2$, the calibration curve for $O_2$ was obtained using amperometry with 6 different concentrations. Similar to performing CV, different concentrations of dissolved oxygen (DO) were prepared by bubbling nitrogen gas into the deionized water to adjust the DO level in the solution, and the resulting $O_2$ concentrations were confirmed by using a commercial oxygen meter (DO6 +, Oakton, USA). The reduction current for $O_2$ was measured with five sample points (n=5) per concentration at the activation voltage vs. Ag/AgCl with a drift less than 5% over 3 min. Due to the average barometric pressure of the experiment location (Fort Collins, Colorado (84.8 kPa)) at 38.5° C., the calibration curve was calculated at 158 μM for 21% dissolved oxygen concentration.

Hydrogen peroxide sensor calibration. Similar to performing CV for $H_2O_2$, the $H_2O_2$ sensor was calibrated with solutions made with phosphate-buffered saline and $H_2O_2$ solution (Sigma-Aldrich, USA). The calibration solutions were prepared by diluting a known $H_2O_2$ concentration solution to the concentrations needed in the calibration. Electrochemical amperometry was used to continuously detect a change of analyte concentration. There were a total of 11 concentrations (3.3 μM, 2.2 μM, 1.5 μM, 970 nM, 645 nM, 400 nM, 267 nM, 178 nM, 119 nM, 79 nM, and 0 nM) used for $H_2O_2$ calibration. The oxidative current was measured with five sample points (n=5) per concentration at the activation voltage vs. Ag/AgCl at 38.5° C. Each measurement was taken when the measured current had a drift less than 5% over 3 min.

Experimental protocol. The multi-sensor glass chip and its assembly were placed in an incubator with the temperature set at 38.5° C. A breakout board with relays was used for electrically isolating the WE in use from the other idling WE. The experiments were carried out initially in the oxygen-saturated Mir05 buffer with 1 μl of isolated mitochondria. A decreasing DO concentration was observed due to the $O_2$ consumption of the mitochondria at their basal state. In order to limit the impact of changes in DO concentration on ROS production, the measurement time for $O_2$ was limited to 5 min. A three-way splitter was used to provide injections of substrates and ADP from two different syringes. To minimize the interference from the diffusion of the ambient oxygen, the outlet was normally closed except for during the injection of substrates or ADP. FIG. 9 shows the experiment setup with different components labeled.

After the sensors reached their steady basal state with a known amount of mitochondria in the microchamber, the mitochondria were first energized with 1 μl of substrates from the syringe through the inlet to boost the $H_2O_2$ production rate. Once a stable oxidation current was observed, the measurement of the sensor device was switched to the $O_2$ channel to measure the corresponding DO level. The mitochondria were then energized with 1 μl of ADP from the other syringe through the inlet to establish stable OXPHOS-linked OCR and ROS production. Finally, the measurement was switched back to the $H_2O_2$ channel after measuring DO level for five minutes.

The conversion from the measured current to HPR and OCR was performed based on the method adapted from [19]:

$$\text{Rate}\ (p\text{mol}\cdot s^{-1}\cdot \text{mg}^{-1}) = \frac{\Delta I/\Delta t}{\Delta I/\Delta C}\times \forall \times N + w$$

where N is the quantity of the mitochondria and w is the weight of the mitochondria added into the chamber. The quantity of the mitochondria is 120,000, and the weight of the mitochondria is 5 μg.

Results and Discussion

Figure 10A:
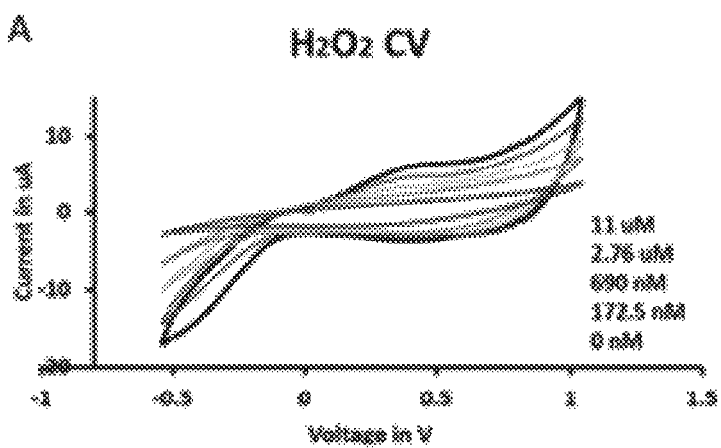
FIGS. 10A-10B. (10A) CV results with various [$H_2O_2$]: 11 μM, 2.76 μM, 690 nM, 172.5 nM, and 0 nM. The oxidative peaks are found at 0.4 V. (10B) Hydrogen peroxide sensor calibration curve: $H_2O_2$ sensor was calibrated from 0 nM to 3.3 μM. The error bars represent standard deviations (n=5) measured at 38.5° C.
Figure 10B:
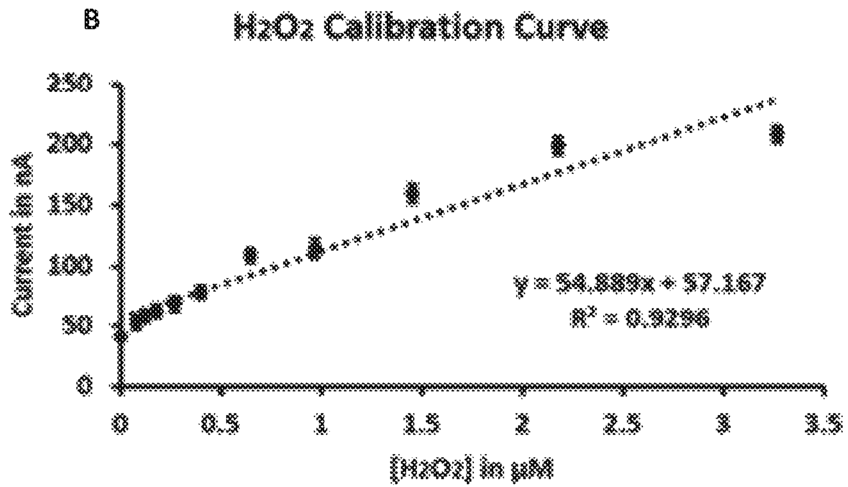

Hydrogen peroxide sensor calibration. Cyclic voltammetry (CV) was performed in the presence of 11 μM, 2.76 μM, 690 nM, 172.5 nM, and 0 nM of hydrogen peroxide from 0.55 V to 1.05 V with a scan rate of 100 $mV\cdot s^{-1}$ to find the activation voltage of the $H_2O_2$ sensor, and the results are shown in FIG. 10(A). An oxidation peak was observed at 0.4 V for the solutions containing $H_2O_2$, and CV did not present any peak when no $H_2O_2$ was present in the solution. Since the $H_2O_2$ concentration produced by mitochondria was expected to be below 3 μM, an activation voltage of 0.4 V vs. Ag/AgCl was chosen as the activation voltage for calibration and was used for measurement. FIG. 10(B) depicts the amperometric measurement results with eleven different concentrations (0 nM, 3.3 μM, 2.2 μM, 1.5 μM, 970 nM, 645 nM, 400 nM, 267 nM, 178 nM, 119 nM, and 79 nM). All CV's and calibrations of the $H_2O_2$ sensor were carried out at 38.5° C., which is the same temperature used in the mitochondria measurement described in this article.

A linear calibration curve for the $H_2O_2$ sensor is shown in FIG. 10(B) using the activation voltage of 0.4 V vs. Ag/AgCl. The amperometric current increases linearly with the increase in $H_2O_2$ concentration, and the sensor sensitivity is 54.889 nA/μM with an $R^2$ value of 92.96%. The calibration data (mean±standard deviation, n=5) are presented as measured current with respect to $H_2O_2$ concentration in μM. The calculated limit of detection (LoD) of the $H_2O_2$ sensor is 58.36 nM [20].

Figure 11A:
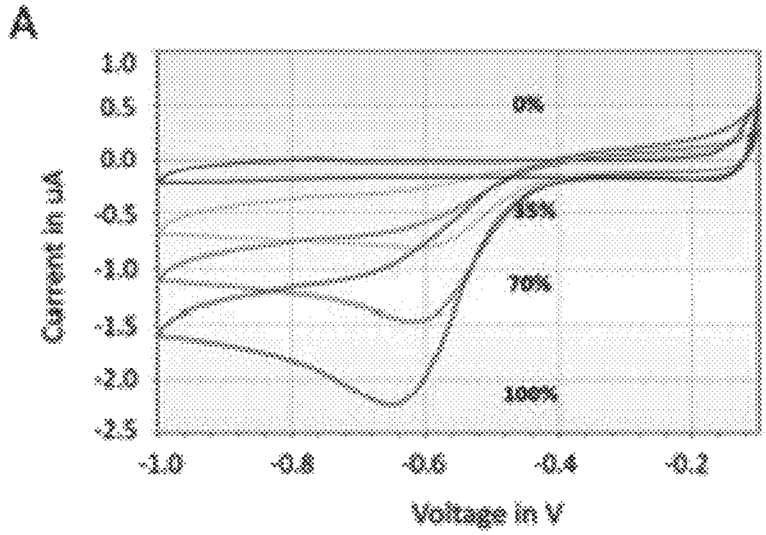
FIGS. 11A-11B. (11A) CV results for $O_2$. The reductive peaks of dissolved oxygen can be found around −0.65 V vs. Ag/AgCl for $O_2$. (11B) Oxygen sensor calibration curve: The error bars represent standard deviations (n=5) measured at 38.5° C.
Figure 11B:
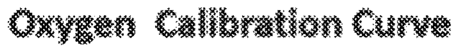
Figure 11B:
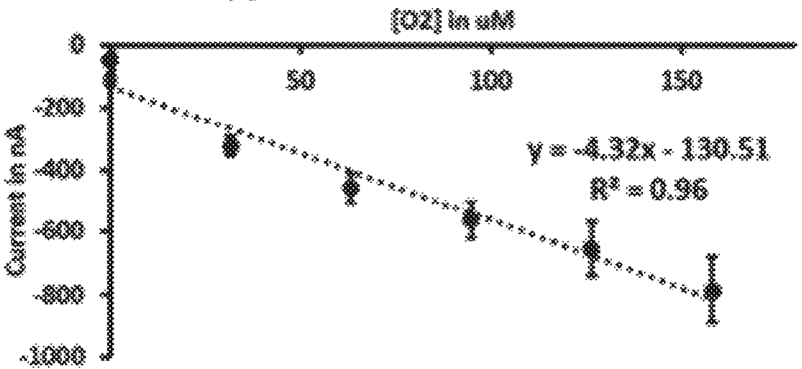

Oxygen sensor calibration. CV experiments with various oxygen concentrations (100%, 70%, 35%, and 0%) were performed with a scan rate of 100 $mV\cdot s^{-1}$. Based on the CV data shown in FIG. 11(A), the activation voltage for $O_2$ amperometry was found to be −0.65 V vs. Ag/AgCl. The results of $O_2$ amperometry under six different DO concentrations (100%, 80%, 60% 40%, 20%, and 0%) were shown in FIG. 11(B) and presented as mean±standard deviation (n=5). The magnitude of the sensor output current increases linearly with the increase of DO concentration. FIG. 11(B) shows the calibration curve of the $O_2$ sensor after converting DO concentration in the chamber from percentage to molarity, where 100% dissolved oxygen concentration represents 158 μM based on the altitude where the experiments were performed. Sensitivity of the $O_2$ sensor when an activation voltage of −0.65 V vs. Ag/AgCl was applied is −4.32 nA/μM with an $R^2$ value of 96%, and its calculated LoD is −143 nA, which is equivalent to 2.9 μM. All CV's and calibrations of the $O_2$ sensor were carried out at 38.5° C., which is the same temperature used in all mitochondria measurements.

Figure 12A:
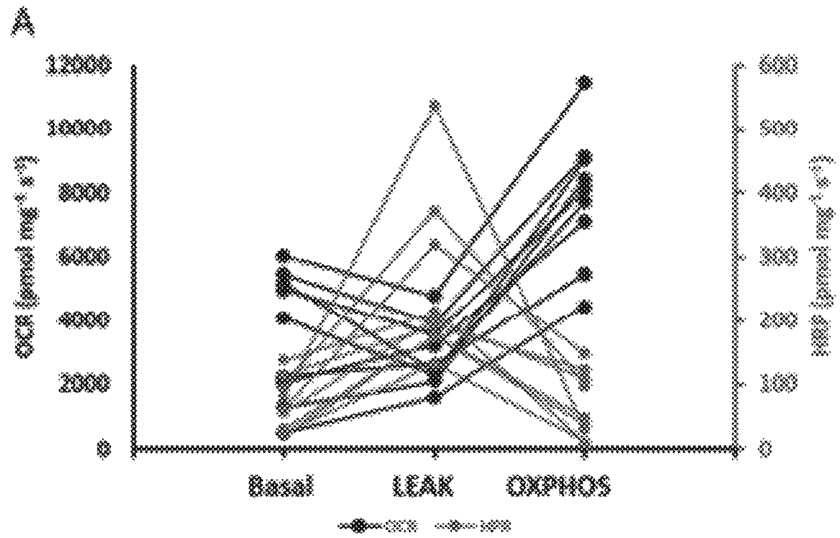
FIGS. 12A, 12B, 12C, 12D. (12A) Values of oxygen consumption rate (OCR, black) and hydrogen production rate (HPR, grey) from rat cardiac preparations during basal, LEAK, and OXPHOS-linked respiration. Rates of (12B) hydrogen production, (12C) oxygen consumption from isolated mitochondria, and (12D) ratios of HPR over OCR during LEAK and OXPHOS-linked respiration. Data are presented as mean±SD (n=9 for both OCR and HPR and * p<0.01).
Figure 12B:
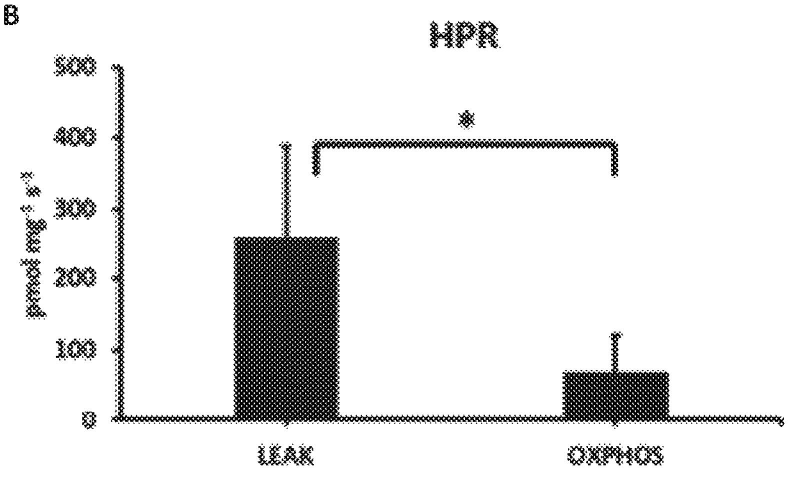
Figures 12C, 12D:
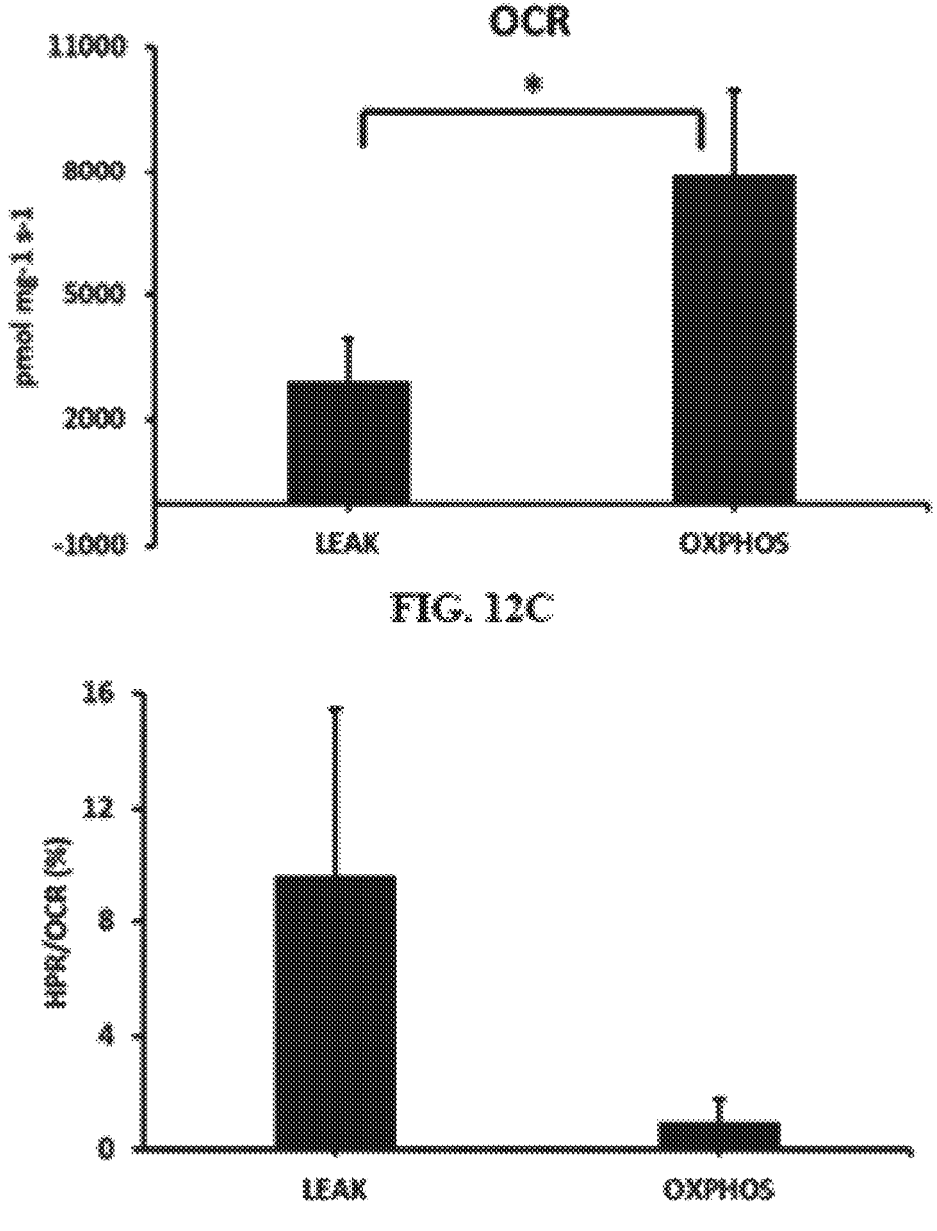

Isolated mitochondria HPR and OCR in LEAK and OXPHOS-linked states. After reaching a stable basal state, the mitochondria were provided substrates to induce maximal non-phosphorylating respiration, commonly referred to as State 4 or LEAK respiration. This was followed by the addition of ADP to maximally fuel the ATP synthase, thus enabling the maximal OXPHOS-linked (or State 3) respiration rate. FIG. 12 shows the changes of HPR and OCR of mitochondria during the transitions from the basal state to the LEAK state, and to the OXPHOS-linked state. OCR did not change significantly from basal to LEAK state (53%). However, it increased 167.94% from 2944.96 $pmol\cdot s^{-1}\cdot mg^{-1}$ to 7890.51 $pmol\cdot s^{-1}\cdot mg^{-1}$ from the LEAK state to the OXPHOS state (FIGS. 12A and 12C), consistent with high respiratory control of cardiac mitochondria by ADP [6]. In contrast, the HPR increased over 350% from the basal state to the LEAK state when mitochondria were energized by substrates (LEAK), then decreased 73.29% from 257.9 $pmol\cdot s^{-1}\cdot mg^{-1}$ to 68.89 $pmol\cdot s^{-1}\cdot mg^{-1}$ ($P<0.01$) following the transition to the OXPHOS state (FIGS. 12A and 12B). This trend is consistent with the strong influence of mitochondrial membrane potential on ROS production by the respiratory chain, which is highest during the LEAK state and dissipated by the activity of ATP synthase in the OXPHOS state [1, 6]. The HPR of the mitochondria was about 9.57% of OCR during LEAK and decreased to 0.95% of OCR during OXPHOS-linked respiration (FIG. 12D), which is similar to the 10-fold decrease in HPR/OCR recently reported from murine cardiac mitochondria using the same protocol using high-resolution fluorespirometry [6]. Taken together, these results demonstrate the expected responses of intact mitochondrial OCR and HPR to respiratory substrates in the presence and absence of ADP, thereby establishing the utility of this novel multi-sensor device for evaluating mitochondrial bio-energetics in very small biological samples.

Importantly, we would like to note that the HPR has a strong relationship with the $O_2$ concentration in the environment [6]. Mitochondria produce more ROS when $O_2$ concentration is high, and vice versa. This can lead to wide variations in HPR measurements as chamber oxygen declines. We observed that the OCR measurement occasionally could not provide a stable reading within five minutes and the measurement for $O_2$ had to be extended for a maximum of 2 more minutes to allow the readings to stabilize. The longer the $O_2$ measurement time was extended, the less $O_2$ was in the environment due to the $O_2$ consumption by the mitochondria. This could partially explain some of the measurement variations shown in FIG. 12.

Applications for simultaneous monitoring of mitochondria HPR and OCR. ROS are inevitable by-products of mitochondrial respiration, which leave mitochondria and intact cells primarily in the form of $H_2O_2$. Excessive ROS production can be damaging to cells and their tissue environment, contributing to the development and progression of major diseases, including cancer and cardiovascular disease. Given their strong interdependence, simultaneous measurement of mitochondrial both OCR and HPR provides a more complete information about cell physiology and pathophysiology. The sensor device in this paper demonstrated its ability to simultaneously monitor changes in $H_2O_2$ and $O_2$ concentrations in a small quantity of isolated cardiac mitochondria during the LEAK and OXPHOS-linked respiration. Results illustrate that the multi-sensor platform has the sufficient sensitivities and linearities necessary for both $H_2O_2$ and $O_2$ to enable advances in instrumentation technology that can improve our understanding of cellular bioenergetics in health and disease.

Integration of $O_2$ and $H_2O_2$ sensors in the current device with other metabolic sensors in the same platform [13, 14] can provide even more complete information about cellular activity and metabolism. For example, although not used in the present study, a pH sensor can be added to provide simultaneous measurement of extracellular acidification rate (ECAR; a surrogate measure of glycolysis) along with OCR and ROS production from the same biological sample. This approach would be particularly useful for investigating metabolic transitions that occur in several cell types in response to stress, such as immune cells that shift from OXPHOS to glycolytic metabolism when activated by antigen or pathogen [21] or in cancer [22]. These transitions are frequently associated with robust changes in cellular ROS production and release [23], but the precise links between these processes are not well understood. In these contexts, simultaneous measurement of OCR and HPR provides an internally-controlled index of ROS release (HPR/OCR) that is particularly useful for studying samples with inherent or unknown variability in mitochondrial content or metabolic activity, such as primary circulating une cell samples [24] and heterogeneous tumor micro-biospies [25].

The following patents, applications, and publications as listed below and throughout this document, are hereby incorporated by reference in their entirety herein.

[1] M. P. Murphy, How mitochondria produce reactive oxygen species, Biochem. J. 417 (2009) 1-13.

[2] T. Nishikawa, E. Araki, Impact of mitochondrial ROS production in the pathogenesis of diabetes Mellitus and its complications, Antioxid. Redox Signal. 9 (2007) 343-353.

[3] O. S. Kornfeld, S. Hwang, M.-H. Disatnik, C.-H. Chen, N. Qvit, D. Mochly-Rosen, Mitochondrial reactive oxygen species at the heart of the matter, Circ. Res. 116 (2015) 1783-1799.

[4] X. Wang, W. Wang, L. Li, G. Perry, H. Lee, X. Zhu, Oxidative stress and mitochondrial dysfunction in Alzheimer's disease, Biochim. Biophys. Acta 1842 (2014) 1240-1247.

[5] G. P. Bienert, J. K. Schjoerring, T. P. Jahn, Membrane transport of hydrogen peroxide, Biochim. Biophys. Acta 1758 (2006) 994-1003.

[6] L. C. Li Puma, M. Hedges, J. M. Heckman, A. B. Mathias, M. R. Engstrom, A. B. Brown, A. J. Chicco, Experimental oxygen concentration influences rates of mitochondrial hydrogen peroxide release from cardiac and skeletal muscle preparations, Am. J. Physio. Regul. Integr. Comp. Physio. 318 (2020) R972-R980.

[7] H.-S. Wong, P. A. Dighe, V. Mezera, P.-A. Monternier, M. D. Brand, Production of superoxide and hydrogen peroxide from specific mitochondrial sites under different bioenergetic conditions, J. Biol. Chem. 292 (2017) 16804-16809.

[8] S. I. Dikalov, D. G. Harrison, Methods for detection of mitochondrial and cellular reactive oxygen species, Antioxid. Redox Signal. 20 (2014) 372-382.

[9] A. A. Starkov, Measurement of mitochondrial ROS production, in: P. Bross, N. Gregersen (Eds.), Protein Misfolding and Cellular Stress in Disease and Aging, Humana Press, Totowa, NJ, 2010, pp. 245-255.

[10] A. Boveris, B. Chance, The mitochondrial generation of hydrogen peroxide. General properties and effect of hyperbaric oxygen, Biochem. J. 134 (1973) 707-716.

[11] G. Krumschnabel, M. Fontana-Ayoub, Z. Sumbalova, J. Heidler, K. Gauper, M. Fasching, E. Gnaiger, Simultaneous High-Resolution Measurement of Mitochondrial Respiration and Hydrogen Peroxide Production, in: V. Weissig, M. Edeas, (Eds.), Mitochondrial Medicine. Methods in Molecular Biology, Humana Press, New York, NY, 2015, pp. 245-261.

[12] M. Makrecka-Kuka, G. Krumschnabel, E. Gnaiger, High-resolution respirometry for simultaneous measurement of oxygen and hydrogen peroxide fluxes in permeabilized cells, tissue homogenate and isolated mitochondria, Biomolecules 5 (2015) 1319-1338.

[13] Y. Obeidat, G. Catandi, E. Carnevale, A. J. Chicco, A. DeMann, S. Field, T. Chen, A multi-sensor system for measuring bovine embryo metabolism, Biosens. Bioelectron. 126 (2019) 615-623.

[14] Y. M. Obeidat, M.-H. Cheng, G. Catandi, E. Carnevale, A. J. Chicco, T. W. Chen, Design of a multi-sensor platform for integrating extracellular acidification rate with multi-metabolite flux measurement for small biological samples, Biosens. Bioelectron. 133 (2019) 39-47.

[15] Y. Obeidat, T. Chen. Characterization of an $O_2$ sensor using microelectrodes, IEEE, 2016, pp. 1-3.

[16] T. Tatsuma, M. Gondaira, T. Watanabe, Peroxidase-incorporated polypyrrole membrane electrodes, Anal. Chem. 64 (1992) 1183-1187.

[17] A. B. Heim, D. Chung, G. L. Florant, A. J. Chicco, Tissue-specific seasonal changes in mitochondrial function of a mammalian hibernator, Am. J. Physio. Regul. Integr. Comp. Physio. 313 (2017) R180-R190.

[18] T. Komlo'di, O. Sobotka, G. Krumschnabel, N. Bezuidenhout, E. Hiller, C. Doerrier, E. Gnaiger, Comparison of mitochondrial incubation media for measurement of respiration and hydrogen peroxide production, in: C. Palmeira, A. Moreno (Eds.), Mitochondrial Bioenergetics. Methods in Molecular Biology, Human Press, New York, NY, 2018, pp. 137-155.

[19] Y. M. Obeidat, A. J. Evans, W. Tedjo, A. J. Chicco, E. Carnevale, T. W. Chen, Monitoring oocyte/embryo respiration using electrochemical-based oxygen sensors, Sens. Actuators B: Chem. 276 (2018) 72-81.

[20] D. A. Armbruster, T. Pry, Limit of blank, limit of detection and limit of quantitation, Clin. Biochem. Rev. 29 (Suppl 1) (2008) S49-S52.

[21] Y. Li, A. Jia, Y. Wang, L. Dong, Y. Wang, Y. He, S. Wang, Y. Cao, H. Yang, Y. Bi, G. Liu, Immune effects of glycolysis or oxidative phosphorylation metabolic pathway in protecting against bacterial infection, J. Cell. Physiol. 234 (11) (2019) 20298-20309.

[22] J. Zheng, Energy metabolism of cancer: Glycolysis versus oxidative phosphorylation, Oncol. Lett. 4 (6) (2012) 1151-1157.

[23] H.-Y. Peng, J. Lucavs, D. Ballard, J. K. Das, A. Kumar, L. Wang, Y. Ren, X. Xiong, J. Song, Metabolic reprogramming and reactive oxygen species in T cell immunity, Front. Immunol. 12 (2021), 652687.

[24] X. Zhang, A. Mardinoglu, L. A. B. Joosten, J. A. Kuivenhoven, Y. Li, M. G. Netea, A. K. Groen, Identification of discriminating metabolic pathways and metabolites in human PBMCs stimulated by various pathogenic agents, Front. Physiol. 9 (2018), 139.

[25] S. Loponte, S. Lovisa, A. K. Deem, A. Carugo, A. Viale, The many facets of tumor heterogeneity: is metabolism lagging behind? Cancers 11 (10) (2019) 1574.

[26] U.S. Pat. No. 11,346,805B2.

[27] U.S. Patent Publication No. US20210318286A1.

[28] U.S. Patent Publication No. US20200324289A1.

What is claimed is:

1. An electrochemical sensing device comprising:

one or more substrates joined to form:

a culture container configured to retain an electrochemical sample, the one or more substrates forming a bottom surface and a side wall surface for the culture container that terminates at a top to define the culture container;

a set of two or more sample containers in operative connection with the culture container through a set of respective channels defined in the one or more substrates, the one or more substrates forming a second bottom surface and a second side wall surface that terminates at a second top to define each of the sample containers, wherein each of the first set of channels has a cross-sectional area at a first end that expands to form each respective sample container and has a cross-sectional area at a second end that expands to form the culture container;

a port in operative connection with the sample containers through a second set of channels defined in the one or more substrates, wherein the first set of channels and the second set of channels are interconnected through the sample container and the culture container to form a differential micro-valve controlled by application of differential pressure and without mechanical moving parts in the channels; and a controller configured to generate a first command to control application of the differential pressure and initiate an analysis sequence of the electrochemical sample;

wherein the controller is configured to control the actuation of a pump to apply a single negative pressure at the port to induce a first pressure differential along a path defined between the first set of channels, through the set of two or more sample containers, to the second set of channels, to cause a portion of the electrochemical sample to flow from the culture container through the first set of channels to the two or more sample containers, wherein the set of two or more sample containers are instrumented to conduct electrochemical analyses of the electrochemical sample and provide signals corresponding to measurements of electrochemical analyses of the electrochemical sample to the controller, and wherein, subsequent to the measurements, the controller is configured to generate a second command to control the actuation of a pump to induce a second pressure differential along the path defined between the first set of channels and the second set of channels to clear the sample container.

2. The electrochemical sensing device of claim 1, wherein the one or more substrates comprise:

a first section comprising at least one sensor or electrode embedded therein, the at least one sensor or electrode embedded therein being located below the culture container, the set of two or more sample containers, or a combination thereof; and a second section comprising microfluidic components defining the culture container, the set of first channels, and the set of two or more sample containers.

3. The electrochemical sensing device of claim 1, wherein the set of two or more sample containers comprises a second sample container in operative connection with the culture container through a third set of respective channels defined in the one or more substrates, the one or more substrates forming a third bottom surface and a third side wall surface that terminates at a third top to define the second sample container, wherein the third channel has a cross-sectional area at a first end that expands to form the second sample container and has a cross-sectional area at a second end that expands to form the culture container.

4. The electrochemical sensing device of claim 3, wherein the second sample container connects to a fourth set of respective channels defined in the one or more substrates, wherein the application of the negative pressure at the port causes a second portion of the electrochemical sample to flow from the culture container through the third set of respective channels to the second sample container.

5. The electrochemical sensing device of claim 1, wherein the set of two or more sample containers comprises a third sample container in operative connection with the culture container through a fifth set of respective channels defined in the one or more substrates, the one or more substrates forming a fourth bottom surface and a fourth side wall surface that terminates at a fourth top to define the third sample container, wherein the fifth set of respective channels has a cross-sectional area at a first end that expands to form the third sample container and has a cross-sectional area at a second end that expands to form the culture container.

6. The electrochemical sensing device of claim 1, wherein the one or more substrates further form a second culture container to retain a second electrochemical sample and a set of one or more sample containers coupled to the second culture container.

7. The electrochemical sensing device of claim 6, wherein the one or more substrates further form a third culture container to retain a third electrochemical sample and a set of one or more sample containers coupled to the third culture container.

8. The electrochemical sensing device of claim 1, further comprising:

stimulus signal generation module comprising a stimulus signal generator circuit in communication with a controller circuit, the stimulus signal generator circuit being configured to generate a stimulus signal for conducting electrochemical analyses of the electrochemical sample.

9. The electrochemical sensing device of claim 1, further comprising:

data acquisition module comprising a data acquisition circuit in communication with a controller circuit, the data acquisition circuit being configured to receive signals corresponding to measurements of electrochemical analyses of the electrochemical sample.

10. The electrochemical sensing device of claim 2, wherein the first section comprises glass or plastic.

11. The electrochemical sensing device of claim 2, wherein the microfluidic components comprise glass or plastic.

12. The electrochemical sensing device of claim 2, wherein the at least one sensor or electrode includes at least one of a pH sensor, a temperature sensor, a dissolved oxygen sensor, a $CO_2$ concentration sensor, hydrogen peroxide sensor, a salinity sensor, a humidity sensor, a pressure sensor, an ammonia sensor, a sugar sensor, an amino acid sensor, a nucleic acid sensor, a nutrient sensor, or a combination thereof.

13. The electrochemical sensing device of claim 1, further comprising a pump, the pump being configured to apply the negative pressure, at the port, different from the culture container to cause the portion of the electrochemical sample to flow from the culture container through the set of first channels to the set of two or more sample containers.

14. The electrochemical sensing device of claim 1, wherein the culture container is configured as an incubation compartment for cell or tissue culturing.

15. The electrochemical sensing device of claim 9, further comprising:

wireless communication module comprising a communication circuit and antenna in communication with a controller circuit, the communication circuit and antenna being configured transmit, to a central data processing system, data corresponding to the measurements of electrochemical analyses of the electrochemical sample.

16. The electrochemical sensing device of claim 1, further comprising;

a housing and a controller circuit, the housing being coupled to the one or more substrates.

17. The electrochemical sensing device of claim 1, wherein the controller is configured to clear content of the sample container back to the culture container.

18. A method of detecting culture parameters comprising:

providing an electrochemical sensing device comprising:

one or more substrates joined to form:

a culture container configured to retain an electrochemical sample, the one or more substrates forming a bottom surface and a side wall surface for the culture container that terminates at a top to define the culture container;

a set of two or more sample containers in operative connection with the culture container through a set of respective channels defined in the one or more substrates, the one or more substrates forming a second bottom surface and a second side wall surface that terminates at a second top to define each of the sample containers, wherein each of the first set of channels has a cross-sectional area at a first end that expands to form each respective sample container and has a cross-sectional area at a second end that expands to form the culture container;

a port in operative connection with the sample container through a second set of channels defined in the one or more substrates, wherein the first set of channels and the second set of channels are interconnected through the sample container and the culture container to form a differential micro-valve controlled by application of differential pressure and without mechanical moving parts in the channels; and a controller configured to generate a first command to control application of the differential pressure and initiate an analysis sequence of the electrochemical sample;

wherein the controller is configured to control the actuation of a pump to apply a single negative pressure at the port to induce a first pressure differential along a path defined between the first set of channels, through the set of two or more sample containers, to the second set of channels, to cause a portion of the electrochemical sample to flow from the culture container through the first set of channels to the two or more sample containers, culturing a cell, tissue, organ, or a combination thereof in the culture container;

acquiring signals from at least one sensor or electrode located in proximity to, or in, the two or more sample containers, wherein the signals are subsequently analyzed to assess the culture parameters; and providing to the controller the acquired signals corresponding to measurements of electrochemical analyses of the electrochemical sample, wherein, subsequent to the measurements, the controller is configured to generate a second command to control the actuation of a pump to induce a second pressure differential along the path defined between the first set of channels and the second set of channels to clear the sample container.

19. The method of claim 18, further comprising:

adding nutrients or test agents to the culture container through a second port at the top of the culture container.

20. The method of claim 18, further comprising:

collecting the electrochemical sample from the two or more sample containers through a third port at the top of each of the sample containers; and returning the collected electrochemical sample to the culture container through a fourth port.

21. The method of claim 19, wherein the culture container is formed of glass or inert material relative to the cell, tissue, organ, nutrients, or test agent.

* * * * *